US010893986B2

(12) United States Patent
Manabe et al.

(10) Patent No.: US 10,893,986 B2
(45) Date of Patent: Jan. 19, 2021

(54) UNDERPANTS-TYPE DISPOSABLE DIAPER WITH REDUCED LATERAL SIDE SEAL TEARING

(71) Applicant: DAIO PAPER CORPORATION, Shikokuchuo (JP)

(72) Inventors: Sadanao Manabe, Tokyo (JP); Akifumi Hayashi, Tokyo (JP); Kosuke Murai, Ehime (JP); Shuichi Ito, Tokyo (JP)

(73) Assignee: Daio Paper Corporation, Ehime (JP)

( * ) Notice: Subject to any disclaimer, the term of this patent is extended or adjusted under 35 U.S.C. 154(b) by 398 days.

(21) Appl. No.: 15/762,749

(22) PCT Filed: Aug. 4, 2016

(86) PCT No.: PCT/JP2016/072991
§ 371 (c)(1),
(2) Date: Mar. 23, 2018

(87) PCT Pub. No.: WO2017/056717
PCT Pub. Date: Apr. 6, 2017

(65) Prior Publication Data
US 2018/0280209 A1    Oct. 4, 2018

(30) Foreign Application Priority Data

Sep. 30, 2015   (JP) .................................. 2015-194546

(51) Int. Cl.
*A61F 13/496*     (2006.01)
*A61F 13/15*      (2006.01)
(Continued)

(52) U.S. Cl.
CPC .... *A61F 13/4963* (2013.01); *A61F 13/15723* (2013.01); *A61F 13/15739* (2013.01);
(Continued)

(58) Field of Classification Search
CPC .. A61F 13/496; A61F 13/4963; A61F 13/515; A61F 13/15723; A61F 13/15739;
(Continued)

(56) References Cited

U.S. PATENT DOCUMENTS 5,562,645 A    10/1996  Tanzer et al.
9,011,404 B2    4/2015  Kobayashi et al.
(Continued)

FOREIGN PATENT DOCUMENTS

EP    2450015 A1    5/2012
JP    H11-506503 A   6/1999
(Continued)

*Primary Examiner* — Michele M Kidwell
(74) *Attorney, Agent, or Firm* — Renner, Kenner; Arthur M. Reginelli

(57) ABSTRACT

An underpants-type disposable diaper includes outer members 12F and 12B having stretchable regions A2 and A3 disposed adjacent to the inner edges of the side seal portions 12A in the width direction. The stretchable regions A2 and A3 include multiple elongated elastically stretchable members 19 disposed between two sheet layers 12S and 12H at predetermined intervals in the front-back direction and extending in the width direction. The elastically stretchable members 19 each include two fixed ends 19*f* fixed to the two sheet layers 12S and 12H, and the section between the fixed ends 19*f* is unfixed to the two sheet layers 12S and 12H. The two sheet layers 12S and 12H are welded into sheet bonding sections 20, at positions between the elastically stretchable members 19 in the stretchable regions A2 and A3 adjacent is the front-back direction. No sheet bonding section protrudes from the side seal portion in the stretchable regions A2 and A3.

5 Claims, 25 Drawing Sheets

(51) Int. Cl.
 *A61F 13/515*  (2006.01)
 *B29C 65/08*  (2006.01)
 *B29C 65/48*  (2006.01)
 *B29C 65/00*  (2006.01)
 *A61F 13/42*  (2006.01)
 *A61F 13/494*  (2006.01)
 *B29K 623/00*  (2006.01)
 *B29L 31/48*  (2006.01)

(52) U.S. Cl.
 CPC .......... *A61F 13/496* (2013.01); *A61F 13/515* (2013.01); *B29C 65/08* (2013.01); *B29C 65/4815* (2013.01); *B29C 66/43* (2013.01); *A61F 13/42* (2013.01); *A61F 13/49413* (2013.01); *A61F 2013/422* (2013.01); *B29K 2623/12* (2013.01); *B29K 2713/00* (2013.01); *B29L 2031/4878* (2013.01)

(58) Field of Classification Search
 CPC ..... B29C 65/4815; B29C 66/43; B29C 65/08; B29L 2031/4878
 See application file for complete search history.

(56) References Cited

U.S. PATENT DOCUMENTS

| | | | |
|---|---|---|---|
| 10,751,228 | B2 * | 8/2020 | Kurohara ................ A61F 13/49 |
| 2006/0270302 | A1 * | 11/2006 | Ando .................. A61F 13/4902 |
| | | | 442/328 |
| 2010/0191212 | A1 * | 7/2010 | Torigoshi .......... A61F 13/49014 |
| | | | 604/385.23 |

FOREIGN PATENT DOCUMENTS

| | | |
|---|---|---|
| JP | 2005-080859 A | 3/2005 |
| JP | 2009-056156 A | 3/2009 |
| JP | 2011-234847 A | 11/2011 |
| JP | 5155839 B | 3/2013 |
| JP | 2013-132526 A | 7/2013 |
| JP | 2013-255560 A | 12/2013 |
| JP | 2014124398 A | 7/2014 |
| JP | 2014-193209 A | 10/2014 |
| JP | 2015-112319 A | 6/2015 |
| WO | 2014103818 A1 | 7/2014 |

* cited by examiner

Fig. 15 (a)
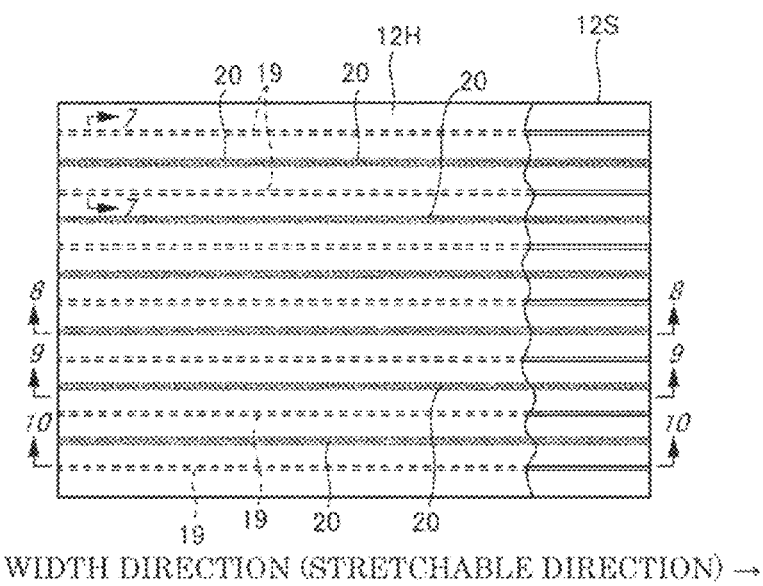
← WIDTH DIRECTION (STRETCHABLE DIRECTION) →
(b)
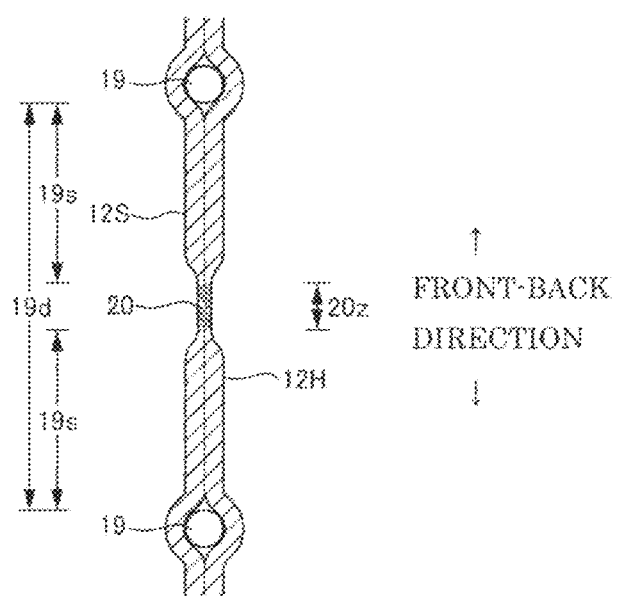

Fig. 19
(a)
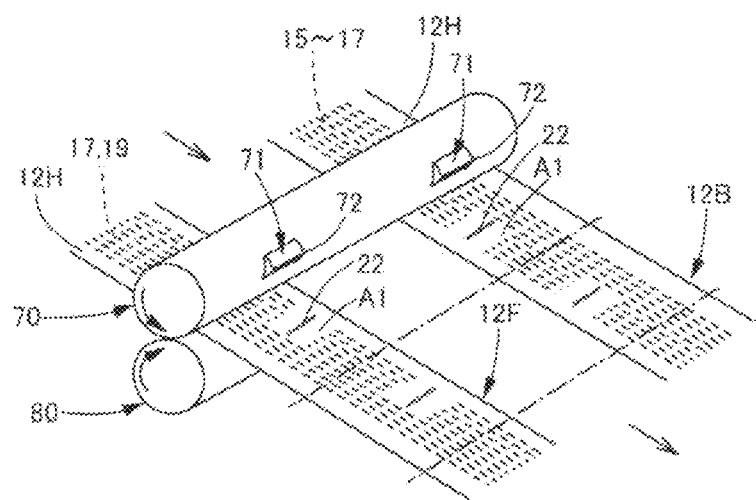
(b)
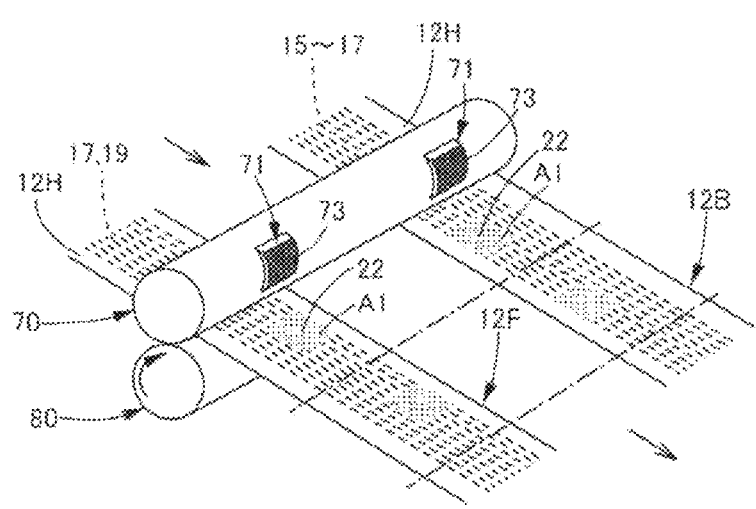

Fig. 20
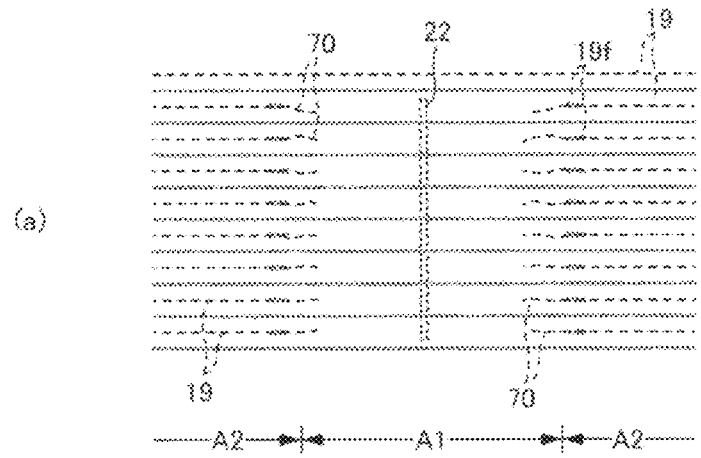
(a)
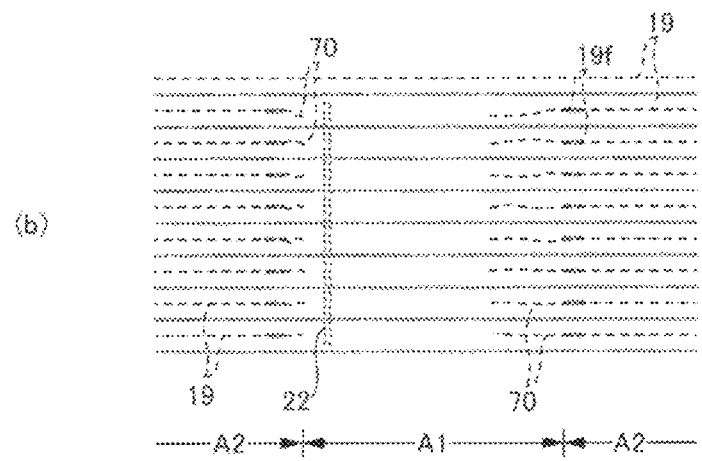
(b)
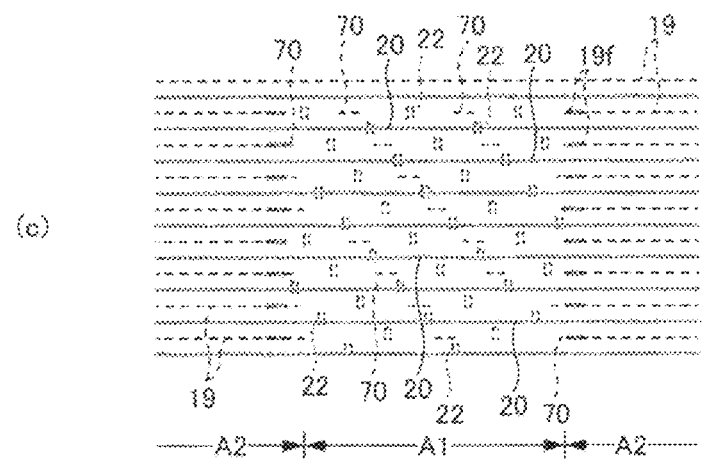
(c)

UNDERPANTS-TYPE DISPOSABLE DIAPER WITH REDUCED LATERAL SIDE SEAL TEARING

TECHNICAL FIELD

The present invention relates to an underpants-type disposable diaper.

BACKGROUND ART

A typical underpants-type disposable diaper includes an outer member including a single segment or two discrete segments and disposed in a front body and a back body and an inner member fixed to the inner face of the outer member from the front body to the back body and containing an absorber, and the two side edges of the outer member in the front body and the two side edges of the outer member in the back body are bonded together into side seal portions defining the waist opening and left and right leg openings. The side seal portions are typically formed by material welding (heat sealing or ultrasonic sealing).

In such an underpants-type disposable diaper, the outer member has a layered structure including several sheet layers and elongated elastically stretchable members, such as rubber threads, fixed in a stretched state between the sheet layers in the width direction to provide a stretchable structure for enhancement of the fit to the body. Some underpants-type disposable diapers having elongated elastically stretchable members fixed in a stretched state in the width direction to a lower torso region defined by a front-back region corresponding to the side seal portions and an intermediate region disposed between the lower torso region in front side and the lower torso region in the back side at predetermined intervals in the front-back direction have a relatively tight fit to the body.

In such a stretchable structure, the means for fixing the elastically stretchable member to the sheet layers and the means for fixing the sheet layers to each other affect the flexibility and cost. Thus, a structure having a reduced fixed area has been proposed. An typical stretchable structure, as illustrated in FIG. 17, is proposed (refer to PTL 1) in which multiple sheet bonding sections 20 are formed by intermittently bonding two sheet lavers 12H and 12S in the width direction and the front-back direction; disposing multiple elongated elastically stretchable members 19 between the two sheet layers 12H and 12S in the non-bonding sections around the sheet bonding sections 20; and fixing only the ends of each elastically stretchable member 19 to the sheet lavers 12H and 12S. In the stretchable structure according to the traditional art, the sheet bonding sections 20 aligned in the front-back direction define grooves extending in the front-back direction, and two sheet layers protrude in opposite directions (from the front and back faces) by approximately the same height to define corrugations 80 in areas between the grooves, to provide a bellows structure as a whole. The corrugations 80 raise in the stretchable direction in a moderately stretched state, whereas the corrugations, which are thin in the stretchable direction, are continuously aligned in the direction orthogonal to the stretchable direction, the material for the corrugations is folded back to form creases such that the tops of the corrugations each have a small radius of curvature, and the corrugations having such creases are aligned at the same height and close to each other in a natural length state. Although the sheet bonding sections 20 may be formed with a hot-melt adhesive, the sheet layers 12H and 12S are often welded (by ultrasonic sealing or heat sealing) with an intent to reduce costs of the material.

Such an underpants-type disposable diaper is removed from the wearer after excretion, for example, by pulling apart the side seal portions between the two side edges of the outer member in the front body and the two side edges of the outer member in the back body. Thus, the side seal portions should have a sealing strength that prevents the side seal portions from tearing while wearing and allows the side seal portions to be readily pulled apart after use.

CITATION LIST

Patent Literature

PTL 1: Japanese Unexamined Patent Application Publication No. 2005-080859

SUMMARY OF INVENTION

Technical Problem

During the research on the shape of the sheet bonding sections, the inventors have discovered an issue that sheet bonding sections protruding from the side edges of the side seal portions toward the center in the width direction cause at least one of the outer member 12F in the front body and the outer member 12B is the back body (the outer member 12F in the front body is illustrated) tears toward the center in the width direction (hereinafter, also referred to as "lateral tear") at the intersection of the side seal portions 12A and the sheet bonding sections 20 before the welding breaks when the side seal portions 12A are pulled apart as illustrated in FIG. 25.

An object of the present invention is to prevent a lateral tear of the side seal portions due to the sheet bonding sections.

Solution to Problem

The present invention, which provides solutions to the issues described above, is described below.

The Invention of Claim 1

An underpants-type disposable diaper comprising:

an outer member disposed in a front body and a back body, the outer member comprising a single segment or two discrete segments; and an inner member disposed from the inner face of the outer member in the front body to the inner face of the outer member in the back body in an intermediate region in the width direction and including an absorber, wherein the two side edges of the outer member in the front body and the two side edges of the outer member in the back body are bonded together into side seal portions defining a waist opening and left and right leg openings, the outer member comprises a stretchable region adjacent to an inner edge of at least one of the side seal portions in the width direction, the stretchable region comprises two sheet layers extending in the width direction and the front-back direction and a plurality of elongated elastically stretchable members extending in the width direction at predetermined intervals in the front-back direction between the sheet layers, the elastically stretchable members each has two fixed ends fixed to the two sheet layers in the stretchable direction, and a free section between the fixed ends, the free section being unfixed to the two sheet layers, the two sheet layers are welded to form at least one sheet bonding section in an inter-free region defined between two adjacent free sections is the front-back direction, and in the stretchable region, no sheet bonding section protrudes from the side seal portion.

Advantageous Effects

According to the present invention, a lateral tear originating at the intersection of the side seal portions and the sheet bonding sections can be prevented when the side seal portions are pulled apart because no sheet bonding section protrudes from the side seal portions.

The Invention of Claim 2

The underpants-type disposable diaper according to claim 1, wherein the sheet bonding section is substantially continuous in the width direction of the inter-free region in the stretchable region.

Advantageous Effects

The inventors, who have conducted experiments on various stretchable structures, have discovered that sheet bonding sections continuously disposed in the width direction in the area between free sections of elastically stretchable members adjacent in the direction orthogonal to the stretchable direction can achieve a soft texture in a natural length state. This result contradicted the common belief that an increase in continuity of the sheet bonding sections, i.e., an increase in the density of the sheet bonding sections causes increased stiffness. In this experiment, sheet bonding sections were actually formed by welding two sheet materials. The individual welded portions were harder than the unwelded portions. However, the surface having a wave pattern in a natural length state was very soft to the touch. This will also be apparent from the experimental results described below.

Although the reason behind this knowledge is unclear, it is presumed that the following structural differences have some effect. In the structure according to the traditional art, corrugations thin in the stretchable direction in a natural length state are continuous in the direction orthogonal to the stretchable direction; the material for the corrugations is folded back to form creases such that the tops of the corrugations each have a small radius of curvature; and the corrugations having such creases are aligned at the same height and close to each other. Thus, the corrugations are barely compressed or fallen down in the thickness direction. Moreover, the tops of the corrugations having a small radius of curvature has coarse feeling when a user touches the tops.

In contrast, if the sheet bonding sections are substantially continuous in the width direction, the two sheet layers only deform in such a manner that the two sheet layers conform with each other. As a result, at a contracted state including a natural length state of the two sheet layers, the two sheet layers conform with each other in a wave pattern and corrugations are formed on the front and back faces thereof, in response to the contraction of the elastically stretchable members. For the two sheet layers conforming with each other in a wave pattern, the tops of the corrugations can curve more gently than those of the traditional art because of not only increased stiffness simply due to the number of sheet layers but also hardening of the sheet bonding sections due to the bonding means and the difference in the curvature between the two sheet layers (the difference is particularly significant in a natural length state). This causes a smooth hand feel and ready compression in the thickness direction, to enhance the softness of the texture. Moreover, in the two sheet layers conforming to each other in a gentle wave pattern, the distance increases between adjacent peaks and adjacent troughs of the wave pattern in the width direction. This reduces the effects of the adjacent peaks and the adjacent troughs respectively supporting each other when the wave pattern is compressed or distorted in the thickness direction. This also is believed to contribute to a softer texture. When a user pinches the front and back faces of a smooth material with his/her fingers, a double layered material gives a feel of greater smoothness than a single layered material to the user even if the material is the same. This is because the frictional resistance between the fingers or between a finger and the material is smaller than the frictional resistance between the layers of the material, and thus the user senses low frictional resistance (smoothness) when pinching the double layered material. The two sheet layers conforming to each other are believed to enhance the feeling of smoothness.

In the present invention, the two sheet layers of the elastically stretchable members have high mobility; hence, the loss of stretching force is small, and natural contraction is achieved even if the stiffness of the sheet layers is uneven (for example, if the fiber density of the non-woven fabric of the sheet layers is uneven). Thus, the volume of the elastically stretchable members to be used can be reduced compared to that in the traditional art.

In such a case where the sheet bonding sections are substantially continuous in the width direction, the sheet bonding sections substantially continuous across the entire width of the outer member facilitates the production device. Unfortunately, in such a case, substantially continuous sheet bonding sections are disposed along the inner edges of the side seal portions in the width direction, and thus the risk of lateral tear becomes significantly high. Thus, the present invention is suitable for a configuration including continuous sheet bonding sections.

The phase "substantially continuous in the stretchable direction" on the sheet bonding sections indicates that the sheet bonding sections are continuous (not disrupted) at least in the direction orthogonal to the stretchable direction (parallel to the two sheet layers in a spread state and orthogonal to the elastically stretchable members), and include not only the sheet bonding sections continuous in the stretchable direction (the two sheet layers are continuously bonded in the stretchable direction) but also the sheet bonding sections intermittently disposed in the stretchable direction (the two sheet layers are intermittently bonded in the stretchable direction).

The Invention of Claim 3

The underpants-type disposable diaper according to claim 2, wherein the sheet bonding section is substantially continuous to an across-the-width position of an intermediate position of the fixed end adjacent to the side seal portion in the width direction, and the end of the sheet bonding section adjacent to the side seal portion is separated from the side seal portion.

Advantageous Effects

Since the fixed ends of the elastically stretchable members also function as bonding means of the two sheet layers, the two sheet layers can be bonded across the entire width of the stretchable regions if the sheet bonding sections between the elastically stretchable members are certainly continuous to the across-the-width positions of the intermediate positions. This is advantageous in that the soft corrugations can be formed across the entire stretchable region.

The Invention of Claim 4

The underpants-hype disposable diaper according to one of claims 1 to 3, wherein at least the fixed end adjacent to the side seal portion is formed by bonding the two sheet layers together and by fixing the elastically stretchable members to the two sheet layers with a hot-melt adhesive continuing across the entire front-back direction of the side seal portion.

Advantageous Effects

The fixed ends of the elastically stretchable members formed with the hot-melt adhesive continuous in the front-back direction form continuous high-strength regions in the inner edge portions of the side seal portions in the width direction so as to enhance the lateral tear resistance.

Advantageous Effects of Invention

As described above, the present invention is advantageous in that lateral tear of the side seal portions due to the sheet bonding sections can be prevented.

BRIEF DESCRIPTION OF DRAWINGS

FIG. 15(a) is an enlarged plan view of essential components of the outer member in a spread state;
and FIG. 15(b) is a cross-sectional view of the outer member taken along line 7-7 in a spread state.
FIG. 19 is a perspective view of a cutter.
FIG. 20 is an enlarged plan view of a non-stretchable region and a stretchable region of the outer member.

DESCRIPTION OF EMBODIMENTS

Figure 1:
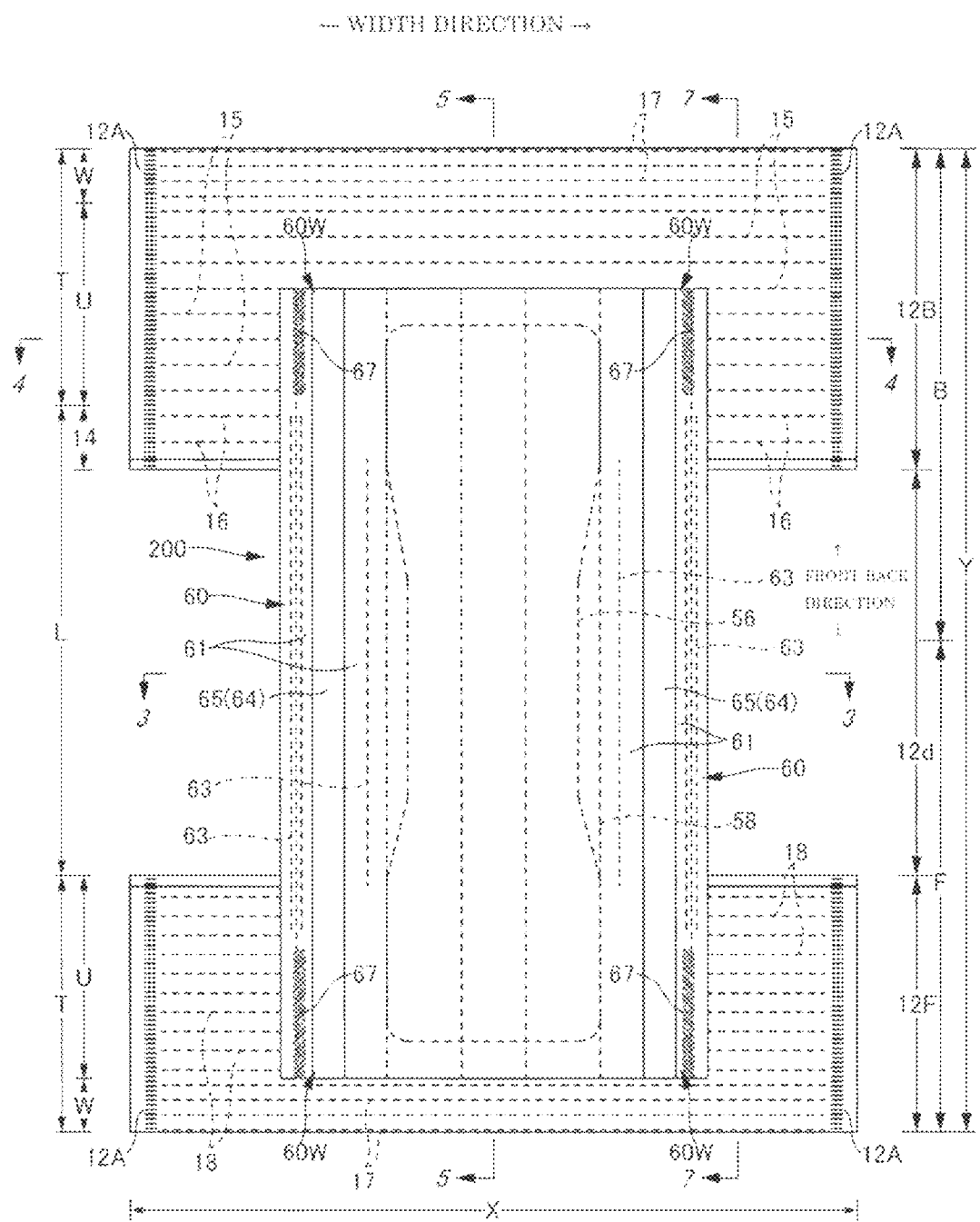
FIG. 1 is a plan view of the inner face of an underpants-type disposable diaper in a spread state.

Embodiments of the present invention will now be described in detail with reference to the accompanying drawings.

FIGS. 1 to 6 illustrate an example underpants-type disposable diaper. The dot patterns in the cross-sections indicate adhesive patterns serving as bonding means of components on the front and back faces. The adhesive patterns are formed through solid, bead, curtain, summit, or spiral application of a hot-melt adhesive or the like, and the fixed portions of the elastically stretchable members are formed through such plication of the adhesive and/or application of the adhesive with a comb gun or a Surewrap nozzle to the circumferential face of the elastically stretchable members. Examples of other bonding means of components may include a fixing means by material welding, such as heat sealing or ultrasonic sealing.

The underpants-type disposable diaper according to this embodiment includes outer members 12F and 12B on a front body F and a back body B, respectively, and an inner member 200 provided on the inner faces of the outer members 12F and 12B and extends from the front body F to the back body B through a crotch portion. The two side of the outer member 12F on the front body F are bonded to the respective edges of the outer member 12B on the back body B, to form side seal portions 12A. The reference sign Y indicates the entire length of the diaper in a spread state (the longitudinal length from the edge of the waist opening WO of the front body F to the edge of the waist opening WO of the back body B), and the reference sign X indicates the maximum width of the diaper in a spread state.

The inner member 200 absorbs and retains excretion, such as urine, and the outer members 12 support the inner member 200 on the body of the wearer. In this embodiment, the upper opening of the outer members 12F and 12B defines the waist opening WO through which the trunk of the wearer passes, and the lower edges of the outer members 12F and 12B and the side edges of the inner member 200 define leg openings LO through which the legs pass at both edges of the inner member 200 in the width direction.

The underpants-type disposable diaper according to this embodiment includes a lower torso region T defined as a longitudinal region including the side seal portions 12A (the longitudinal regions from the waist opening WO to the upper edges of the leg openings LO) and an intermediate region L defined as a front-back region forming the leg openings LO (the region between the longitudinal region including the side seal portion 12A of the front body F and the longitudinal region including the side seal portion 12A of the back body B). The lower torso region T can be conceptually separated into a "waist portion" W forming the edge of the waist opening and an "under-waist portion" U disposed below the waist portion W. Usually, in the case where the lower torso region T includes boundaries undergoing variations in expansion and contraction stress along the width direction (for example, variations in the fineness or the stretch rate of the elastically stretchable members), the area between the boundary closest to the waist opening WO and the waist opening WO is defined as the waist portion W. In the case where such boundaries are absent, the area between an absorber 56 or the inner member 200 and the waist opening WO is defined as the waist portion W. The longitudinal lengths of such portions depend on the dimensions of the product and can be appropriately determined. For example, the longitudinal length may be within the range of 15 to 40 mm for the waist portion W and 65 to 120 mm for the under-waist portion U. The two side edges of the intermediate region are curved into a U-shape or C-shape to fit around the legs of the wearer and define openings through which the legs of the wearer pass. As a result, the underpants-type disposable diaper in a spread state has an overall shape similar to the outline of an hourglass.

(Outer Members)

Figure 9:
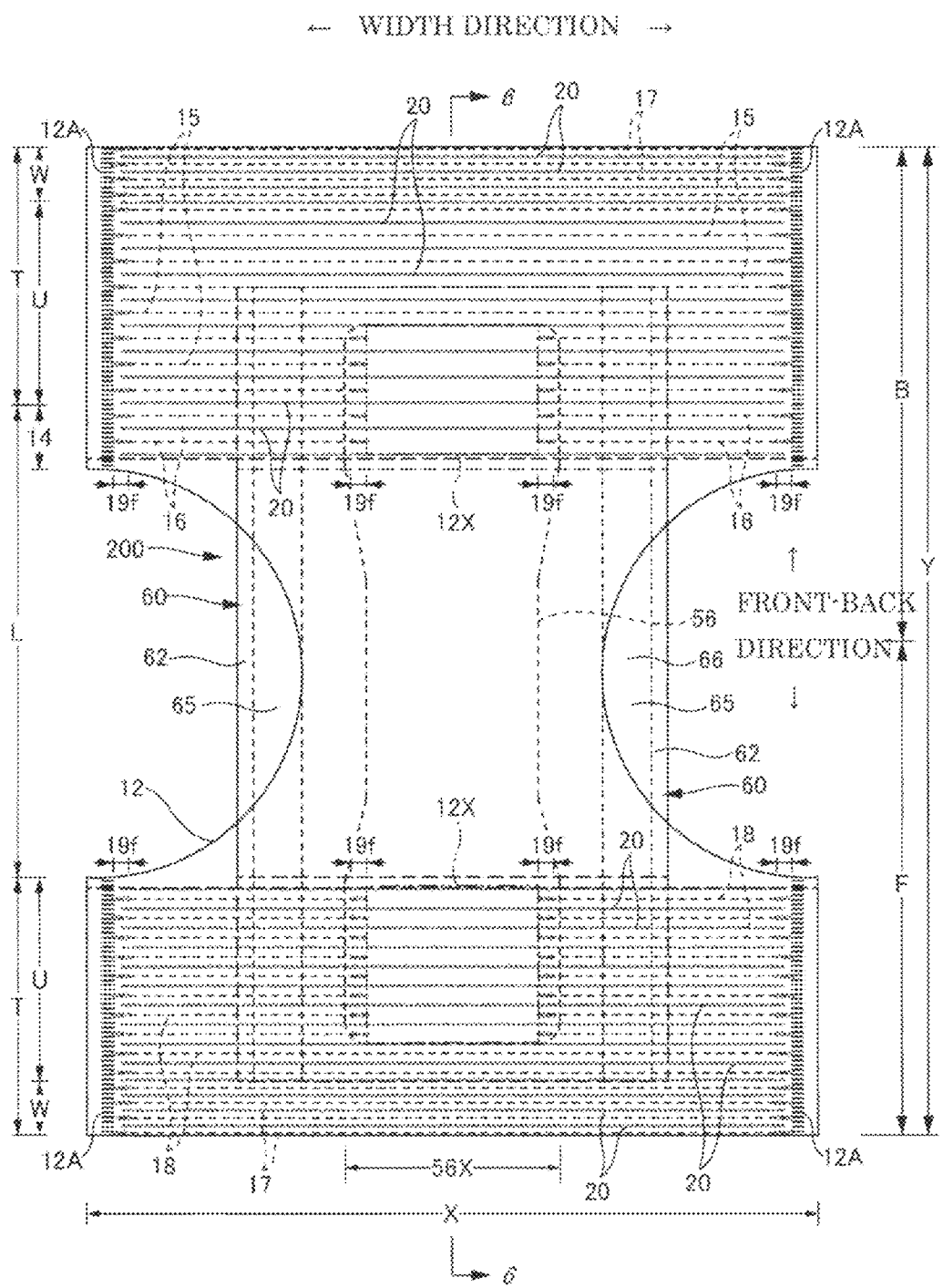
FIG. 9 is a plan view of the external face of the underpants-type disposable diaper in a spread state.

The outer members 12F and 12B, respectively, function as a front outer member 12F in the front body F and a back outer member 12B in the back body B. The front outer member 12F and the back outer member 12B are discontinuous or separated in the regions adjacent to the legs. The distance of separation. 12d may be within the range of approximately 150 to 250 mm. Although not illustrated, a crotch cover sheet composed of non-woven fabric may be bonded to the entire inner member 200 or a section of the back face of the inner member 200 exposed through the separation (the section extending in the front-back direction of the exposed inner member 200 between the front outer member 12F and the back outer member 12B without reaching the front-back edges of the inner member 200 and extending in the width direction without reaching both side edges of the inner member 200, for example). Alternatively, the outer members 12 may be a single segment of the front body F and the back body B through the crotch portion, as illustrated FIGS. 9 and 10. That is, the outer members 12F and 12B in the front body F and the back body B, respectively, are separated as two discrete segments in the former configuration, whereas the outer members 12 in the front body F and back body B are unified as the single segment in the latter configuration.

The outer members 12F and 12B have waist portions, respectively, corresponding to the lower torso region T extending in the longitudinal direction. In this embodiment, the front outer member 12F has no portion corresponding to the intermediate region L, whereas the back outer member 12B has a gluteal cover portion 14 extending from the lower torso region T into the intermediate region L. Although not illustrated, the front outer member 12F may also be provided with an inguinal cover portion extending from the lower torso region T into the intermediate region L; the front outer member 12F may be provided with an inguinal cover portion and without a gluteal cover portion; or both the front outer member 12F and the back outer member 12B may be free from portions corresponding to the intermediate region L. In the illustrated embodiments, the lower edge of the gluteal cover portion 14 is a straight line extending in the width direction, like the lower edge of the front outer member 12F. Alternatively, the lower edge of the gluteal cover portion 14 may be curved such that the outer ends of the lower edge in the width direction are closer to the waist opening.

Figure 3:
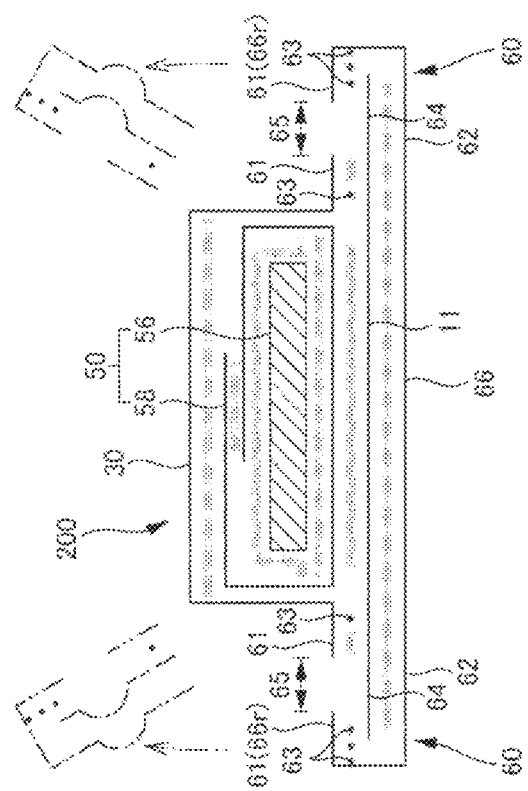
FIG. 3 is a cross-sectional view taken along line 3-3 in FIG. 1.
Figure 4:
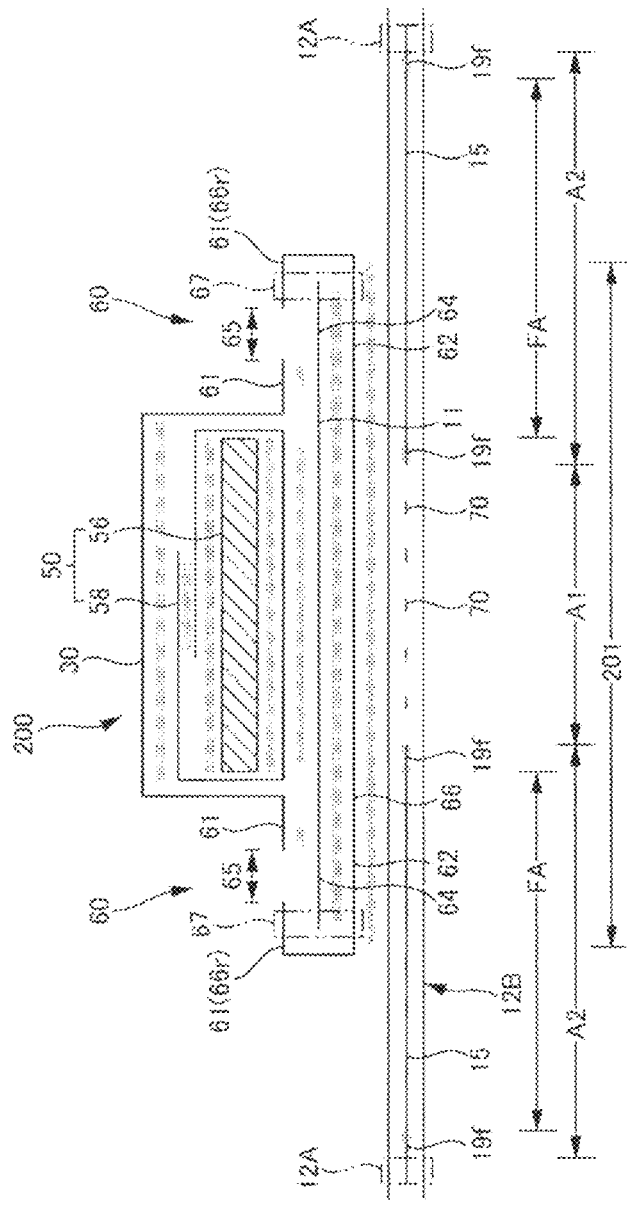
FIG. 4 is a cross-sectional view taken along line 4-4 in FIG. 1.
Figure 5:
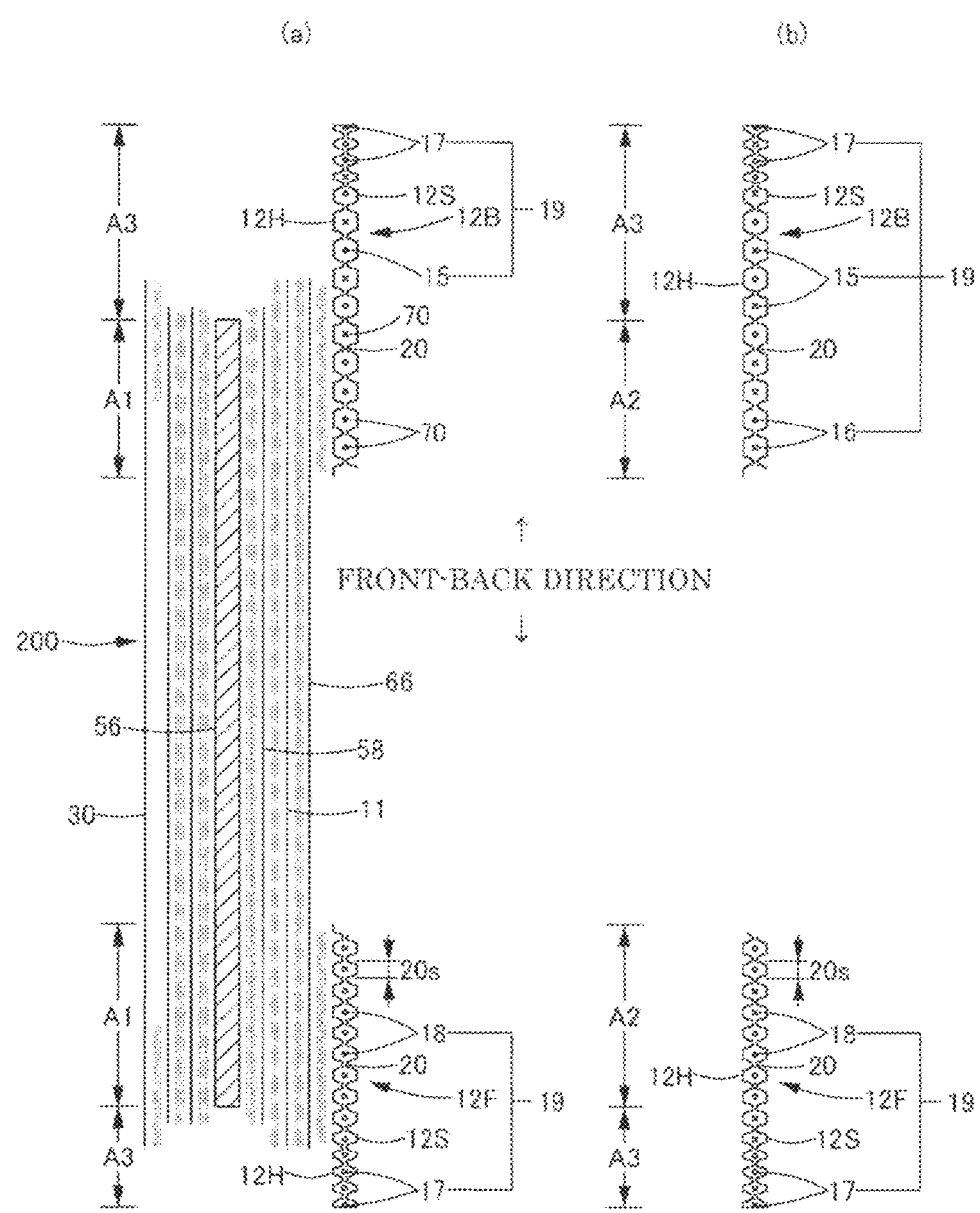
FIG. 5 is a cross-sectional view taken along line 5-5 in FIG. 1.
Figure 10:
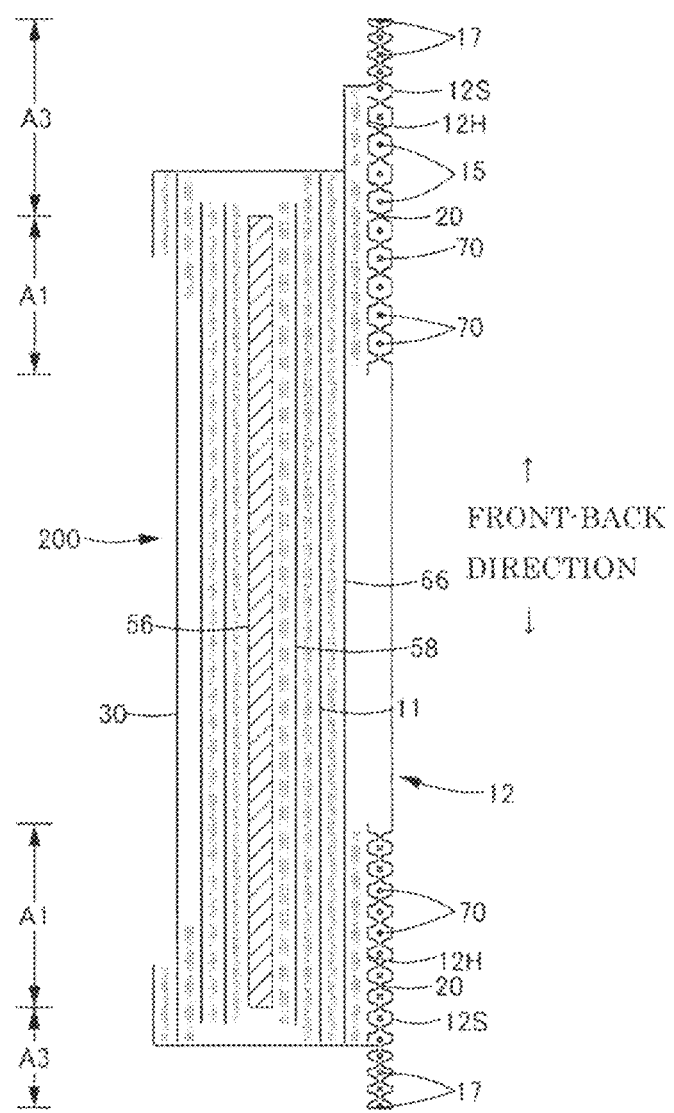
FIG. 10 is a cross-sectional view taken along line 6-6 in FIG. 9.

The outer members 12F and 12B are each provided with an outer sheet layer 12S and an inner sheet layer 12H on the front face and back face, respectively, as illustrated in FIGS. 2 to 5. The outer sheet layer 12S and the inner sheet layer 12H are composed of a single sheet material folded such that the crease is positioned adjacent to the waist opening, as illustrated in FIG. 5. Alternative y, the outer sheet layer 12S and the inner sheet layer 12H may be composed of two sheet materials bonded together, as illustrated in FIG. 10. At least one of the outer sheet layer 12S and the inner sheet layer 12H may include a portion composed of a sheet material different from that of the other portions.

The outer sheet layer 12S and the inner sheet layer 12H may be composed of any sheet material, preferably non-woven fabric. The non-woven fabric may be composed of any raw fibers. Examples include synthetic fibers, such as olefin fibers i.e., polyethylene fibers and polypropylene fibers, polyester fibers, and polyamide fibers; recycled fibers, such as rayon and cupra; natural fibers, such as cotton; and mixed fibers and composite fibers composed of two or more of these fibers. If the sheet bonding sections 20 are to be formed through welding, non-woven fabrics composed of olefin fibers are preferred. The non-woven fabrics may be produced through any process. Examples of known processes include spunlacing, spunbonding, thermal bonding, melt blowing, needle punching, air through bonding, and point bonding. From a viewpoint of softness, a spundonded non-woven fabric composed of polypropylene fiber is particularly preferred for the outer sheet layer 12S and the inner sheet layer 12H. The outer sheet layer 12S and the inner sheet layer 12H may be composed of different sheet materials.

For use of non-woven fabric, the preferred fineness is within the range of approximately 1 to 3 dtex, and the preferred basis weight is within the range of approximately 10 to 30 g/m$^2$. Thus, the preferred total basis weight of the non-woven fabric of the outer members 12F and 12B is within the range of approximately 20 to 60 g/m$^2$. The mean frictional coefficient MIU of the non-woven fabric based on Kawabata's Evaluation System for Fabrics (KES) is 0.30 or smaller, preferably within the range of 0.05 to 0.20 (in both the machine direction: MD and cross direction: CD); the fluctuation of mean frictional coefficient MMD is 0.01 or smaller, preferably within the range of 0.003 to 0.008 (in both the MD and CD); and the thickness under a load of 0.5 g/cm$^2$ is within the range of 0.05 to 0.25 mm, preferably 0.10 to 0.20 mm. The MIU and the MMD can be measured with a Friction Tester KES-SE manufactured by Kato Tech Co., Ltd.

The outer members 12F and 12B have continuous stretchable regions A3 extending from the absorber 56 toward the waist opening continuously in the width direction; and non-stretchable regions A1 disposed in intermediate areas in the width direction and intermittent stretchable regions A2 disposed adjacent to the respective non-stretchable regions A1 in the width direction, in the front-back region including the absorber 56. The elongated elastically stretchable members 19 (15 to 18), such as rubber threads, are fixed between the outer sheet layer 12S and the inner sheet layer 12H in the continuous stretchable region A3 and the intermittent stretchable regions A2 at a predetermined stretch rate in the width direction in a manner stretchable in the width direction (i.e., the width direction is the stretchable direction). The elongated elastically stretchable members 19 may be composed of either synthetic rubber or natural rubber. In part or all of the front-back region including the non-stretchable regions A1 and the intermittent stretchable regions according to the illustrated embodiments, the continuous stretchable regions A3 may be disposed over the entire width, or the front-back region included in the non-stretchable regions A1 according to the illustrated embodiments may be extended toward the waist or the crotch.

More specifically, in the illustrated embodiments, multiple waist elastically stretchable members 17 are stretched and continuously fixed over the entire width between the outer sheet layer 12S and the inner sheet layer 12H in the waist portion W of the outer members 12F and 12B, respectively, at predetermined intervals in the front-back direction at predetermined stretch rate in the width direction. Among the waist elastically stretchable members 17, one or more of the members disposed in the regions adjoining the under-waist portion U may overlap the inner member 200 or may be disposed adjacent to the inner member 200 in the width direction, avoiding the intermediate area overlapping the inner member 200 in the width direction. Each waist elastically stretchable member 17 is preferably composed of approximately 3 to 22 rubber threads having a fineness within the range of approximately 155 to 1880 dtex, specifically 470 to 1240 dtex (synthetic rubber) (for natural rubber, the cross-section is within the range of approximately 0.05 to 1.5 m$^2$, specifically 0.1 to 1.0 mm$^2$) fixed at intervals within the range of approximately 5 to 20 mm, specifically 8 to 16 mm, at a stretch rate within the range of approximately 150% to 400%, specifically 220% to 320%. The waist elastically stretchable members 17 may have different finenesses and stretch rates. For example, the fineness and stretch rate of the elastically stretchable members may differ in the upper and lower areas in the waist portion W.

Under-waist elastically stretchable members 15 and 18 composed of elongated elastically stretchable members are stretched and continuously fixed over the entire width of the outer members 12F and 12B, respectively, in areas of the under-waist portion U above and adjacent of the respective non-stretchable regions A1 in the width direction, avoiding the non-stretchable regions A1, between the outer sheet layer 12S and the inner sheet layer 12H at predetermined intervals in the front-back direction and a predetermined stretch rate in the width direction. The under-waist elastically stretchable members 15 and 18 are each approximately 5 to 30 rubber threads having a fineness within the range of approximately 155 to 1880 dtex, specifically 470 to 1240 dtex (synthetic rubber) (for natural rubber, the cross-section is within the range of approximately 0.05 to 1.5 mm$^2$, specifically 0.1 to 1.0 mm$^2$) fixed at intervals within the range of approximately 5 to 20 mm, specifically 8 to 16 mm, at a stretch rate within the range of approximately 200% to 350%, specifically 240% to 300%.

Multiple cover elastically stretchable members 16 composed of elongated elastically stretchable members are stretched and fixed over the entire width of areas adjacent to the relevant non-stretchable region A1 in the width direction, avoiding to the non-stretchable region A1, between the outer sheet layer 12S and the inner sheet layer 12H of the gluteal cover portion 14 of the back outer member 12B, at predetermined intervals in the front-back direction at a predetermined stretch rate in the width direction. Each cover elastically stretchable member 16 is preferably composed of approximately two to ten rubber threads having a fineness within the range of approximately 155 to 1880 dtex, specifically 470 to 1240 dtex (synthetic rubber) (for natural rubber, the cross-section is within the range of approximately 0.05 to 1.5 mm$^2$, specifically 0.1 to 1.0 mm$^2$) at intervals within the range of approximately 5 to 20 mm, specifically 8 to 16 mm, at a stretch rate within the range of approximately 150% to 300%, specifically 180% to 260%. In the case where an inguinal cover portion is to be provided on the front outer member 12F, the cover elastically stretchable members may be provided in a similar manner.

As in the intermittent stretchable regions A2 according to the illustrated embodiments, the elastically stretchable members 19 (the under-waist elastically stretchable members 15 and 18 and the cover elastically stretchable members 16 according to the illustrated embodiments) of the outer members 12F and 12B fixed in the areas adjacent to the non-stretchable regions A1 in the width direction, avoiding the non-stretchable regions A1, prevent contraction in the with direction of the absorber 56 in the non-stretchable regions A1. Thus, it is preferred that the non-stretchable regions A1 be defined as intermediate areas in the width direction partially or completely overlaying the absorber 56 in the width direction (preferably includes an entire inner-outer fixing portion 201) and the intermittent stretchable regions A2 be defined as areas between edges of the non-stretchable regions A1 in the width direction and the respective side seal portions 12A.

(Fixed Portion of Elastically Stretchable Members)

With reference to FIGS. 2, 9, and 11 to 14, the two ends in the width direction of each elastically stretchable member 19 in the continuous stretchable region A3 and the intermittent stretchable regions A2 are fixed ends 19*f* fixed to the outer sheet layer 12S and the inner sheet layer 12H, and the section between the fixed ends 19*f* is a free section 19*m* unfixed to the outer sheet layer 12S and the inner sheet layer 12H. The free section 19*m* of the elastically stretchable member 19 is freely stretchable in the width direction and shiftable in the front-back direction (the direction orthogonal to the stretchable direction) within the spaces between the sheet bonding sections 20, as described below.

In detail, in the illustrated embodiments, the fixed ends 19*f* of the elastically stretchable members 19 disposed adjacent to areas of the outer members 12F and 12B in the width direction partially or entirely overlaying the inner member 200 are the two ends of the respective elastically stretchable members 19 adjacent to these areas in the width direction, whereas the fixed ends 19*f* of the elastically stretchable members 19 disposed over the entire width of the outer members 12F and 12B are the two ends of the respective elastically stretchable members 19 in the width direction of the outer members 12F and 12B.

Figure 12:
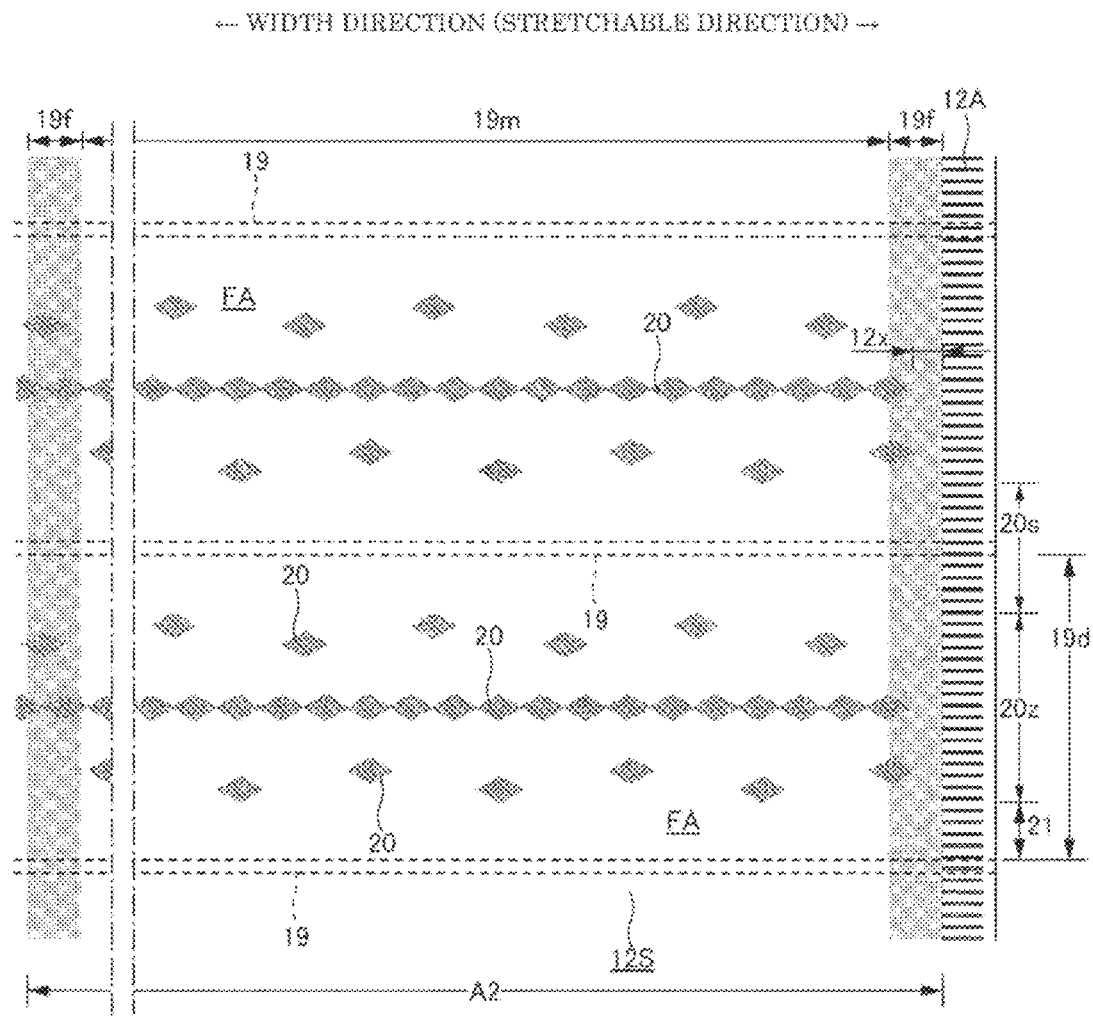
FIG. 12 is an enlarged plan view of essential components of the external face of the outer member.
Figure 13:
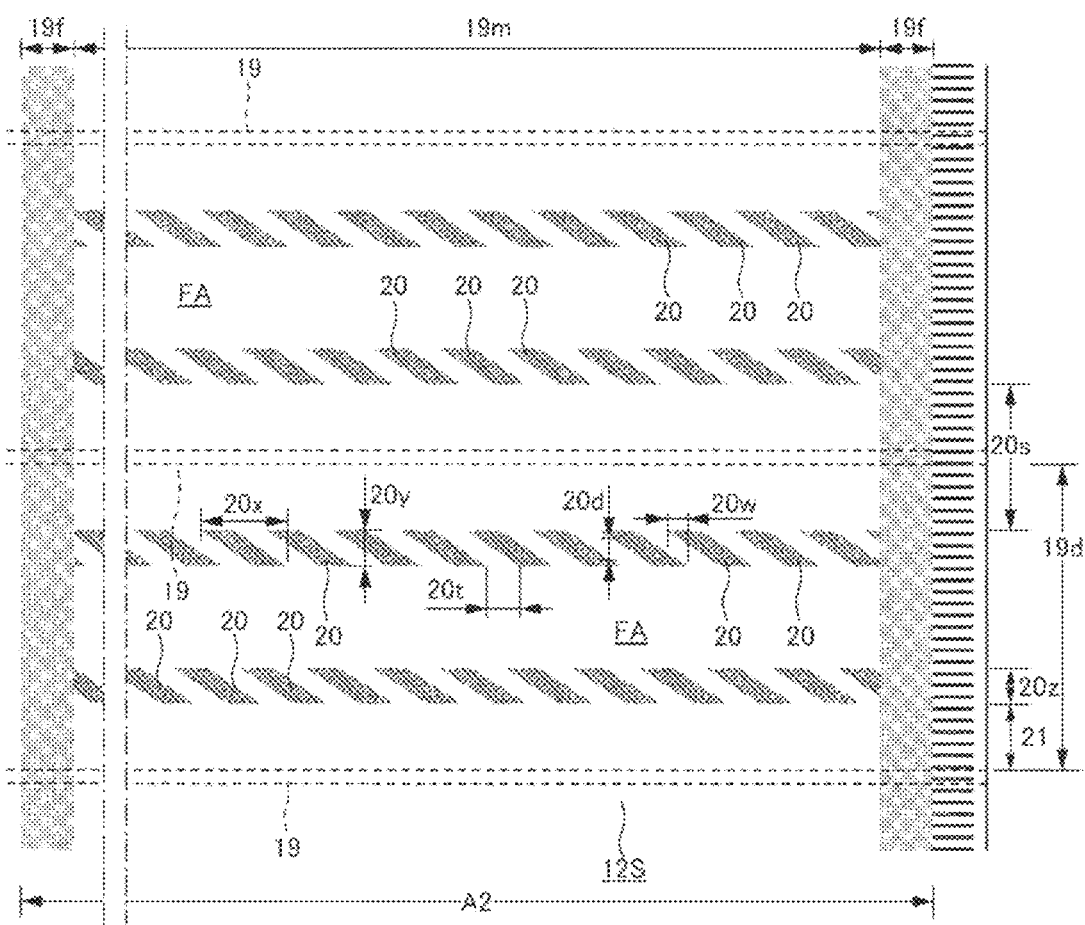
FIG. 13 is an enlarged plan view of essential components of the external face of the outer member.

Any known fixing means may be used to fix the fixed ends 19*f* so as to fix the elastically stretchable members 19 to the outer sheet layer 12S and the inner sheet layer 12H. It is preferred to use a hot-meld adhesive. A hot-melt adhesive is applied to only the end portions of the elastically stretchable members 19, as illustrated in FIGS. 2, 9, 11, and 14. Alternatively, the hot-melt adhesive may be applied in a continuous pattern in the front-back direction across the ends of multiple elastically stretchable members 19, as illustrated in FIGS. 12 and 13. In the latter case, a hot-melt adhesive continuously applied across the entire front-back region of the side seal portions 12A forms continuous high-strength regions in the inner edge portions of the side seal portions 12A in the width direction so as to enhance lateral tear resistance.

The hot-melt adhesive for fixing the fixed ends 19f applied to at least one of the outer sheet layer 12S and the inner sheet layer 12H. Alternatively, the hot-melt adhesive may be applied to only the end portions of the elastically stretchable members 19 with an application means, such as a comb gun or a Surewrap nozzle, to only the circumferential surfaces of the end portions of the elastically stretchable members 19.

The fixed ends 19f adjacent to the side seal portions 12A preferably adjoin the side seal portions 12A, as in the illustrated embodiments. Alternatively, the fixed ends 19f may be separated from the inner edges of the side seal portions 12A in the width direction.

(Sheet Bonding Sections in Stretchable Regions)

Figure 2:
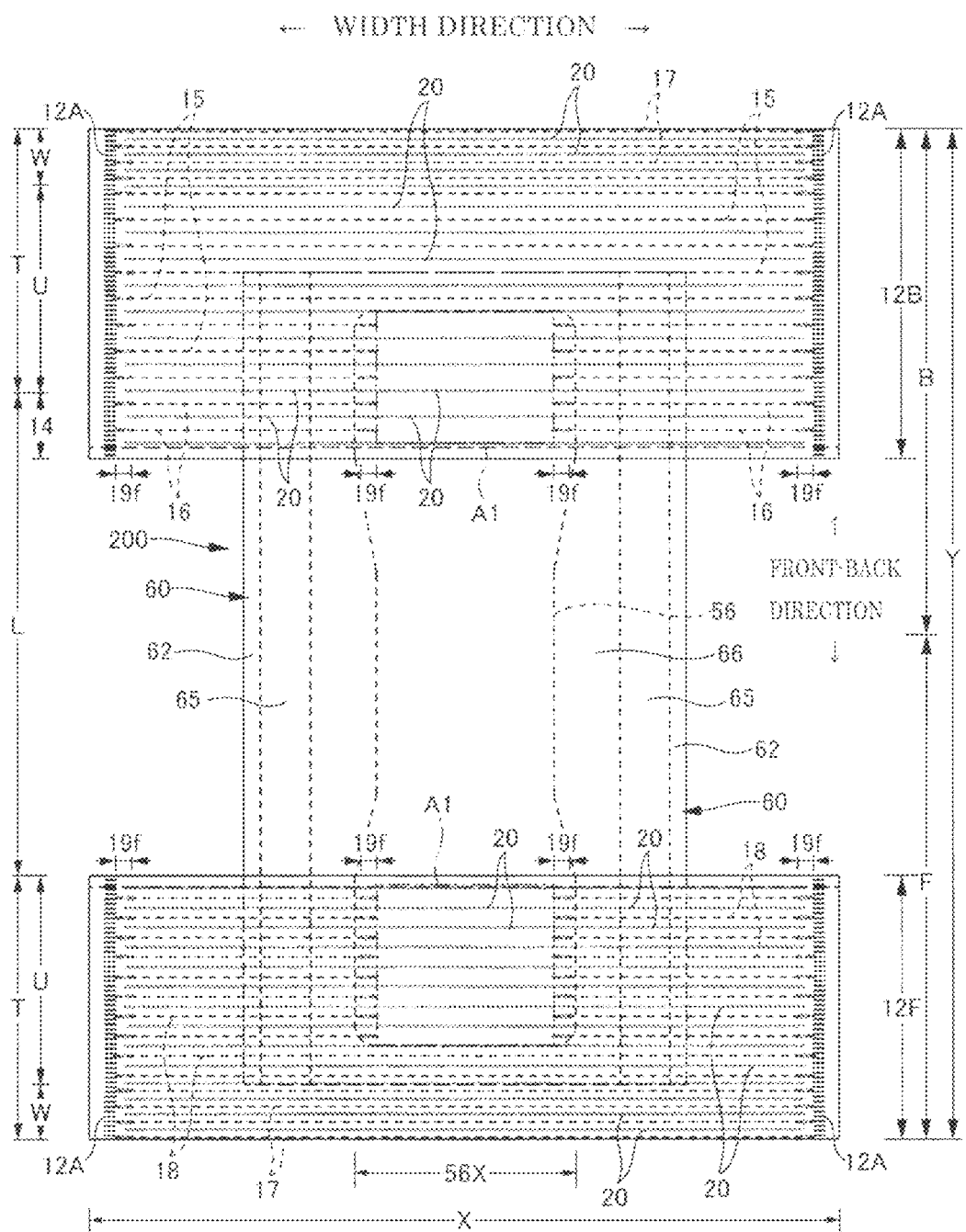
FIG. 2 is a plan view of the external face of the underpants-type disposable diaper in a spread state.
Figure 11:
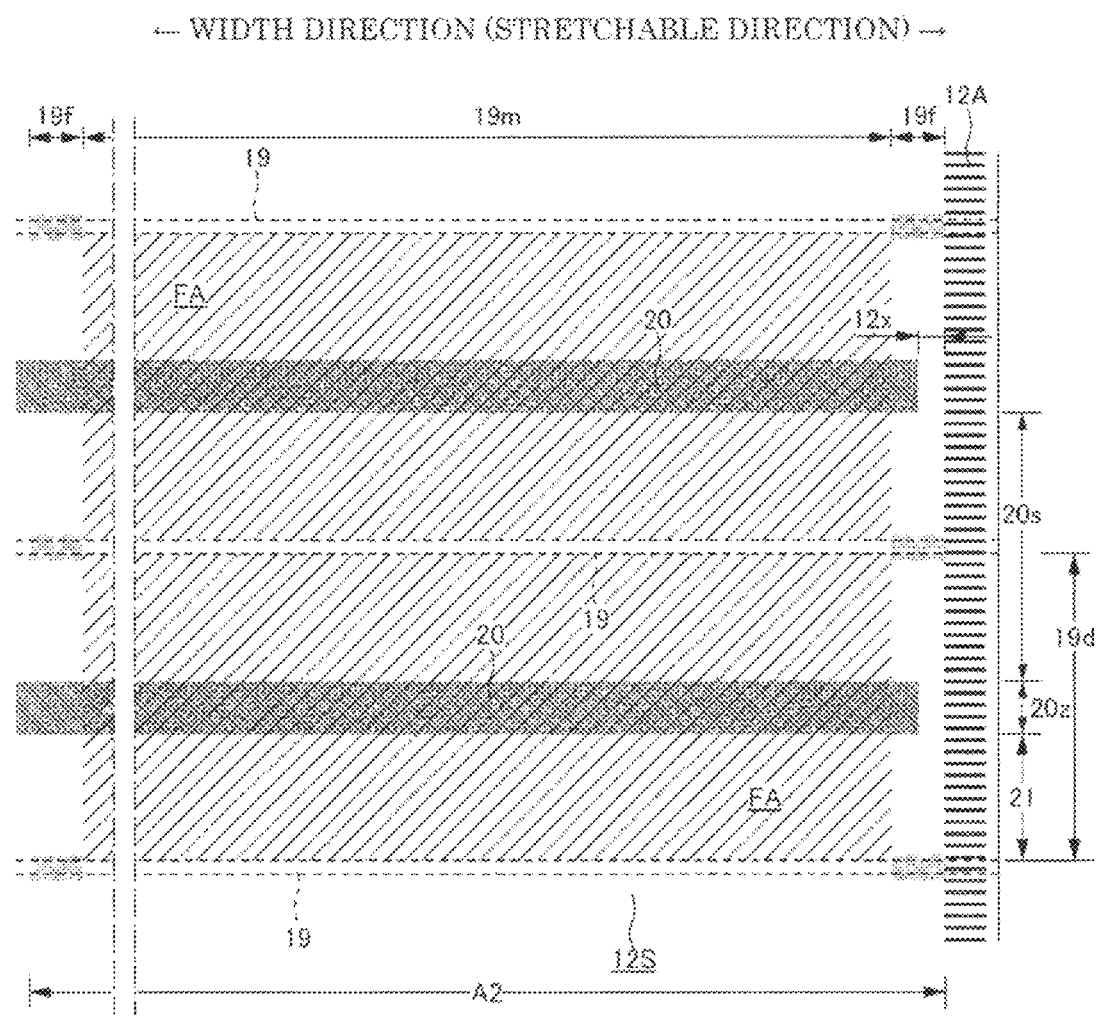
FIG. 11 is an enlarged plan view of essential components of the external face of the outer member.

With reference to FIGS. 2, 5, and 11, inter-free regions FA defined between the free sections 19m of the elastically stretchable members 19 adjacent to each other in the front-back direction (the hatched areas in FIG. 11, which are omitted in other drawings) each include the sheet bonding sections 20 formed through bonding of the outer sheet layer 12S and the inner sheet layer 12H. The sheet bonding sections 20 are formed through welding of the outer sheet layer 12S and the inner sheet layer 12H by ultrasonic sealing or heat sealing. With reference to FIGS. 2, 6, 9, 11 to 14, and 21 to 24, the substantially continuous ends of the sheet bonding sections 20 adjacent to the side seal portions 12A are disposed separated from the side seal portions 12A as indicated by reference sign 12x. As a result, no sheet bonding sections 20 protrudes from the side seal portions 12A. Thus, lateral tears (see FIG. 25) originating at the intersections of the side seal portions 12A and the sheet bonding sections 20 do not occur when the side seal portions 12A at the front outer member 12F and the back outer member 12B are pulled apart.

The distance of separation 12x between the sheet bonding sections 20 and the side seal portions 12A may be any appropriate distance, usually preferred to be approximately 2 to 10 mm.

The length 20z in the front-back direction of an area including the sheet bonding sections 20 in each inter-free region FA may be within the range of 5% to 100% of the front-back interval 19d of adjacent fixed ends 19f in the front-back direction (i.e., the front-back intervals of the elastically stretchable members 19), preferably 5% to 50%. This corresponds to a specific length preferably within the range of 0.5 to 10 mm.

In a spread state of the intermittent stretchable regions A2 and A3, it is preferred that unhanded regions 21 free from the sheet bonding sections 20 are continuously disposed in the width direction in the two edge portions of the inter-free regions FA in the front-back direction, to allow free shift of the free sections 19m of the elastically stretchable members 19 in the front-back direction (the direction orthogonal to the stretchable direction) within the areas between the sheet bonding sections 20, thereby providing a stretchable structure with excellent fit. In specific, the elastically stretchable members 19 and the sheet bonding sections 20 in a spread state are disposed over the entire width, apart from each other in the front-back direction, as illustrated in FIGS. 11 to 14. Since the elastically stretchable members 19 are shiftable in the front-back direction in the areas between adjacent sheet bonding sections 20, the intermediate portions of the elastically stretchable members 19 may shift in the front-back direction after the diaper is worn in a normal state or in a natural length state and come into contact with the sheet bonding sections 20. The front-back length of the unhanded regions 21 may be appropriately determined. This length may be within the range of 10% to 49% of the front-back interval 19d of the fixed ends 19f adjacent in the front-back direction, preferably 25% to 49%. This corresponds to a specific length within the range of 2 to 12 mm, preferably 4 to 9 mm.

The sheet bonding sections 20 may have any wave pattern on the two sheet layers 12S and 12H conforming to each other in a contracted state. For the two sheet layers 12S and 12H to maintain a wave pattern and form soft corrugations on the front and back surfaces while conforming to each other in a contracted state, the unity of the sheet layers 12S and 12H should be maintained at a certain level. For example, as in the traditional art illustrated in FIG. 17, in the case where the areas free from the sheet bonding sections 20 are continuously aligned in the direction orthogonal to the stretchable direction (back-front direction in the illustrated embodiments), the two sheet layers 12S and 12H expand and move apart from each other in the areas free from the sheet bonding sections 20. In contrast, the two sheet layers 12S and 12H in an integrated body inevitably conform to each other in a wave pattern.

Figure 14:
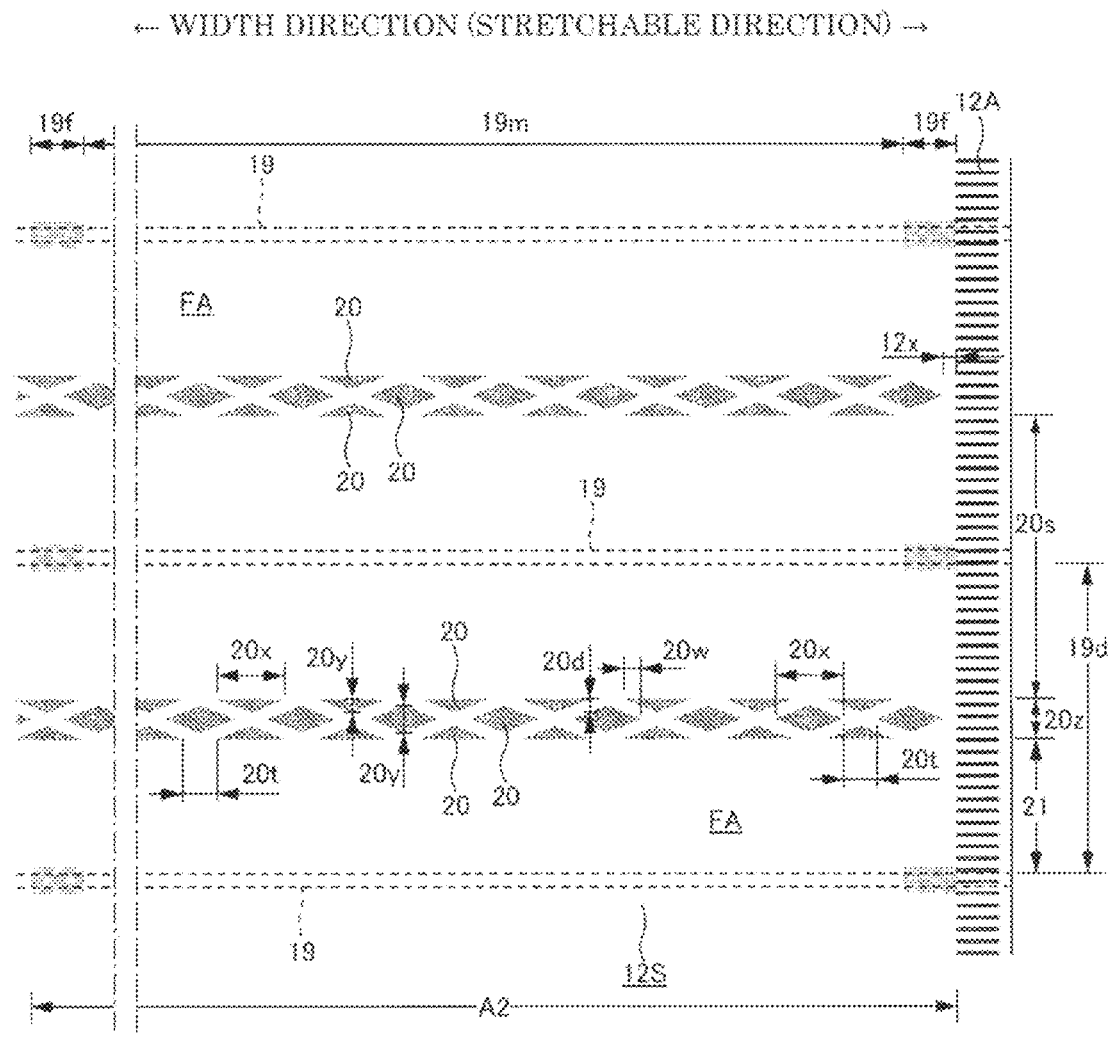
FIG. 14 is an enlarged plan view of essential components of the external face of the outer member.

From such a view point, the sheet bonding sections 20 in a preferred pattern are substantially continuous in the width direction in the inter-free region FA (in other words, the sheet bonding sections 20 are in the form of substantially continuous lines or strips in the inter-free region FA), as illustrated in FIGS. 11 to 14 and 21 to 23. In such a case, the sheet bonding sections 20 should be substantially continuous in the inter-free region FA in the width direction but cannot be readily aligned with the ends of the inter-free FA (the inner edges of the fixed ends 19f in the width direction) as illustrated in FIG. 13. Thus, it is preferred to dispose the sheet bonding sections 20 substantially continuously in the width direction to an across-the-width position of an intermediate position of the fixed end adjacent to the side seal portion 19f in the width direction so that the ends of the sheet bonding sections 20 adjacent to the side seal portions 12A are separated from the side seal portions 12A, as illustrated in FIGS. 11, 12, and 14. Since the fixed ends 19f of the elastically stretchable members 19 also functions as bonding means of the two sheet layers 12S and 12H, the two sheet layers 12S and 12H can be bonded across the entire width direction of the stretchable regions A2 and A3 if the sheet bonding sections 20 between the elastically stretchable members 19 are certainly continuous to the intermediate positions.

Figure 16:
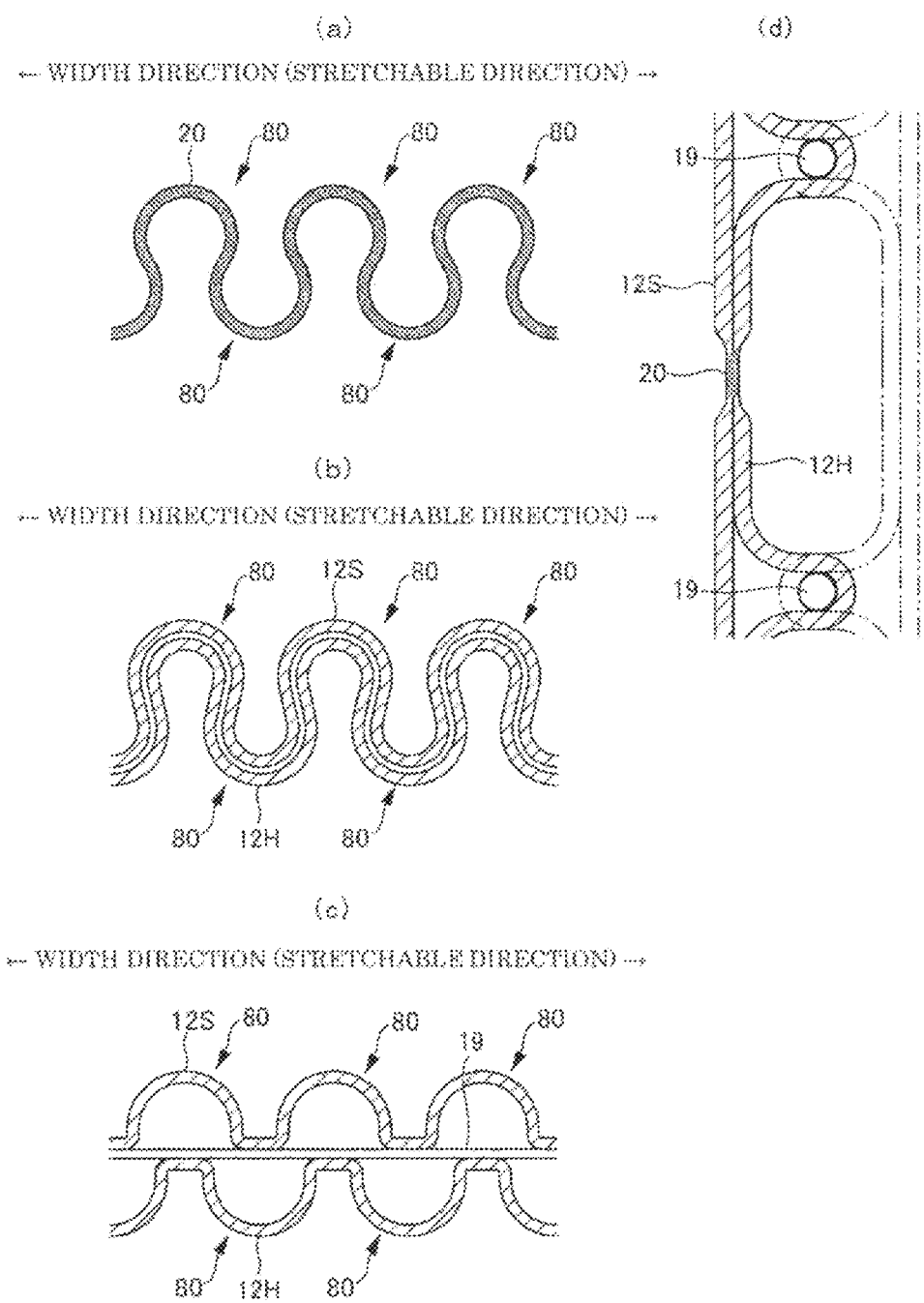
FIG. 16(a) is a cross-sectional view of the outer member taken along line 8-8 in a natural length state.
FIG. 16(b) is a cross-sectional view of the outer member taken along line 9-9 in a natural length state.
FIG. 16(c) is a cross-sectional view of the outer member taken along line 10-10 in a natural length state.
FIG. 16(d) is a cross-sectional view of the outer member taken along line 7-7 in a natural length state.

The stretchable regions A2 and A3 of the outer members 12F and 12B having such configurations include the sheet bonding sections 20 substantially continuous in the stretchable direction. Thus, the two sheet layers 12S and 12H in a natural length state only deform in such a manner that the two sheet layers conform to each other, as illustrated in FIG. 16. As a result, the two sheet layers 12S and 12H in a contracted state, including a natural length state, due to contraction of the elastically stretchable members 19 form a wave pattern in which the two sheet layers 12S and 12H conform to each other, thereby forming the corrugations 80 on the front and back faces. The portion indicated by the dash-double dot lines in FIG. 16(d) are the corrugations 80 disposed in an opposite direction adjacent to the corrugations 80 indicated by the solid lines.

For the two sheet layers 12S and 12H conforming with each other in a wave pattern as illustrated in FIG. 16, the tops of the corrugations 80 can curve more gradually than those of the traditional art because of increased stiffness simply due to the number of sheet layers and the difference in the curvature of the two sheet layers 12S and 12H (the difference is particularly significant in a natural length state). This causes a smooth hand feel and ready compression in the thickness direction, to enhance the softness of the texture. Moreover, in the two sheet layers 12S and 12H conforming with each other in a gentle wave pattern, the distance increases between adjacent peaks and adjacent troughs of the wave pattern in the stretchable direction. This reduces the effect of the adjacent peaks and the adjacent troughs respectively supporting each other when the wave pattern is compressed or fallen down in the thickness direction. This also is believed to contribute to a softer texture.

Figure 17:
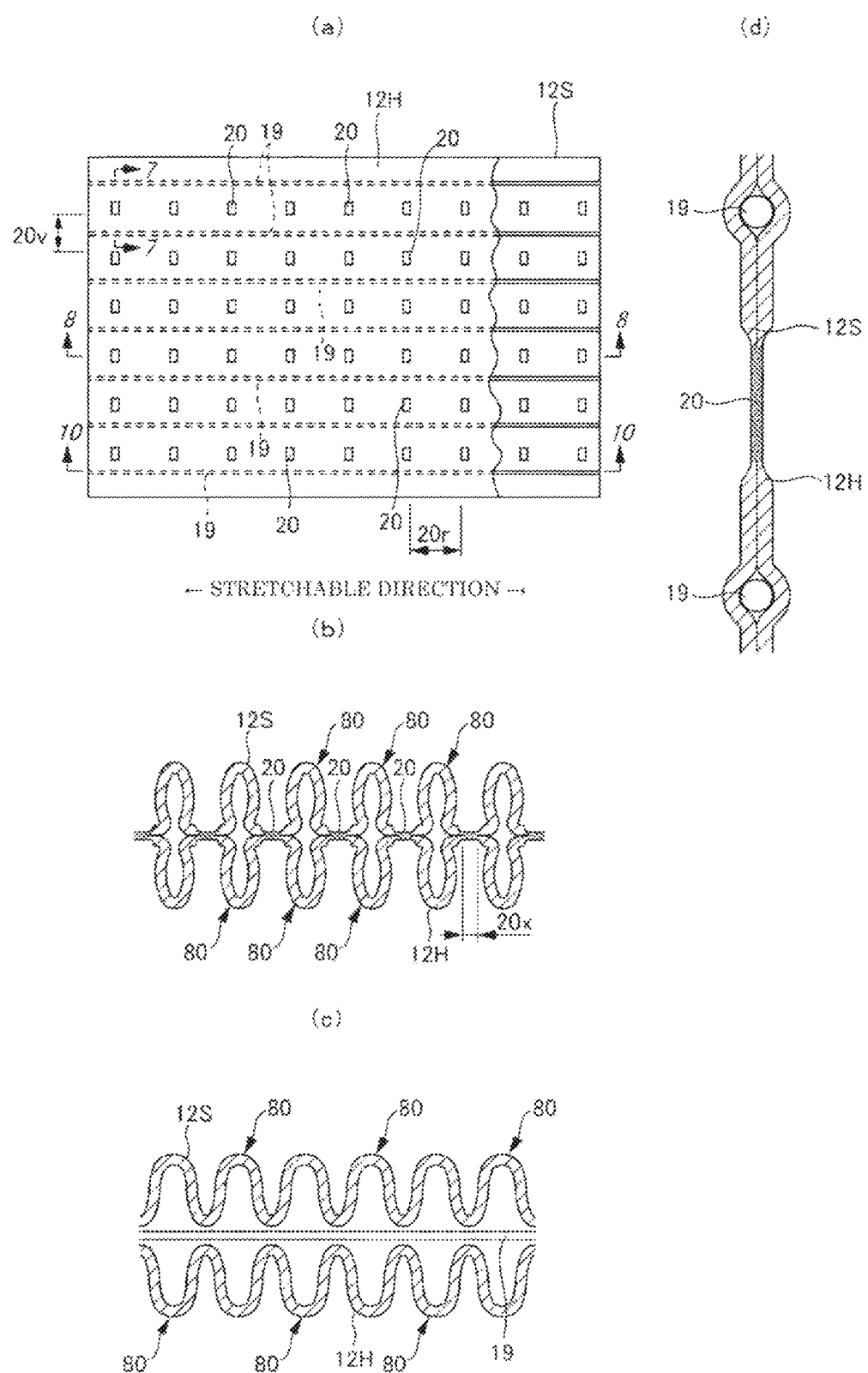
FIG. 17(a) is an enlarged plan view of essential components of the outer member in a spread state.
FIG. 17(b) is a cross-sectional view of the outer member taken along line 8-8 in a natural length state.
FIG. 17(c) is a cross-sectional view of the outer member taken along line 10-10 in a natural length state.
FIG. 17(d) is a cross-sectional view of the outer member taken along line 7-7 in a natural length state.
Figure 18:
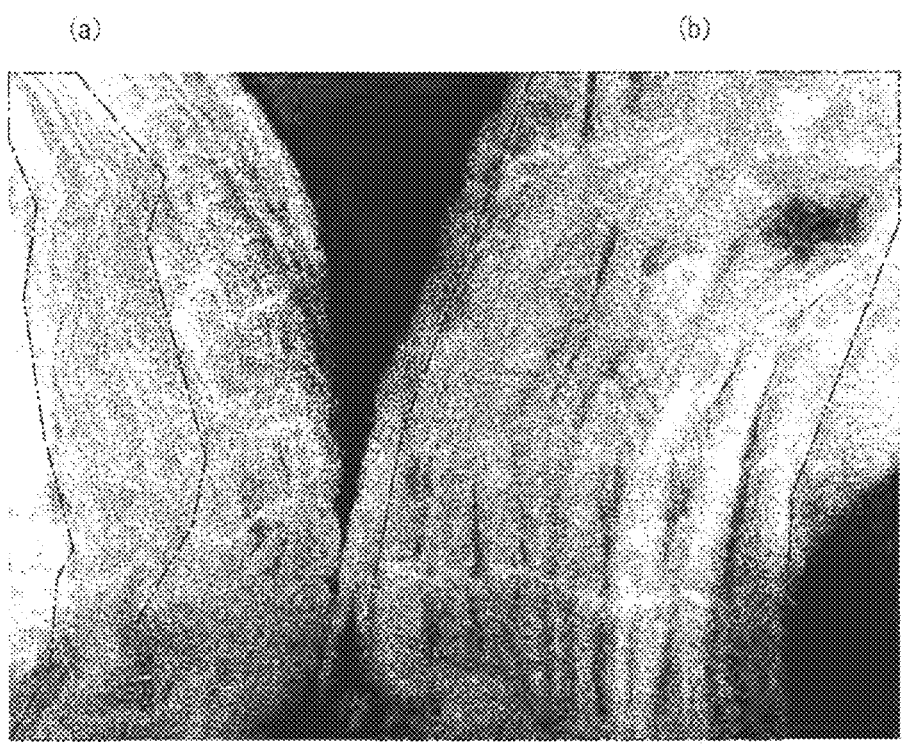
FIG. 18 is a photograph indicating a comparison of stretchable structures of a sample according to the present invention with a commercially available product.
Figure 21:
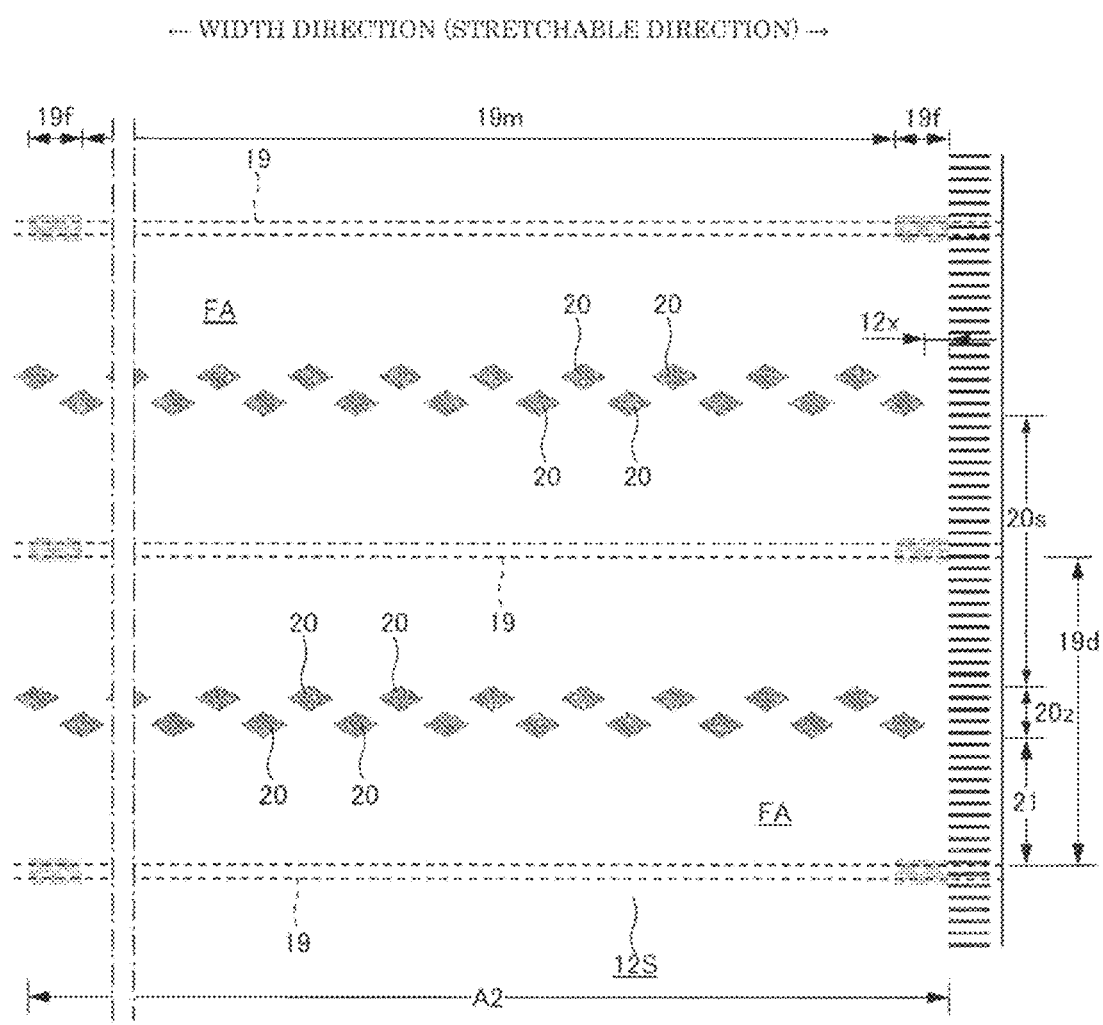
FIG. 21 is an enlarged plan view of essential components of the outer member in a spread state.

This is also apparent through a comparison of the stretchable structure of the conventional sample depicted in the area defined by the dash-double dot lines in FIG. 18(a) and the stretchable structure of the sample according to the present invention in the area defined by the dash-double dot lines in FIG. 18(b). The stretchable structure of the conventional sample in the area defined by the dash-double dot lines is the same as that illustrated in FIG. 17.

In the case where the front and back faces of a smooth material are pinched between fingers, a double layered material feels smoother than a single layered material, even if the material is the same. This is because the frictional resistance between the fingers or between a finger and the material is smaller than the frictional resistance between the layers of the material, and thus low frictional resistance (smoothness) is sensed when a double layered material is pinched. Two sheet layers conforming to each other are believed to enhance the sense of smoothness. Thus, the preferred frictional characteristics of the sheet material for the two sheet layers 12S and 12H are as described above.

Figure 22:
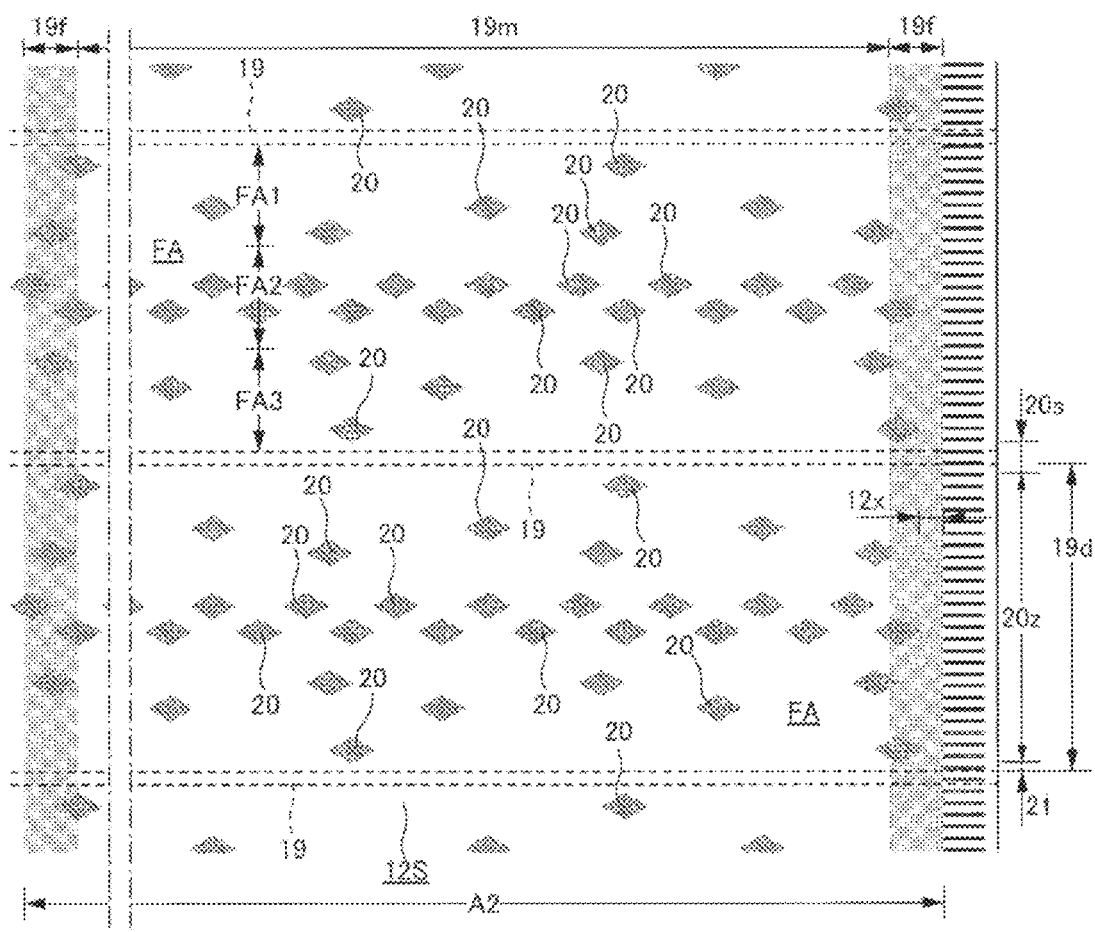
FIG. 22 is an enlarged plan view of essential components of the outer member in a spread state.
Figure 23:
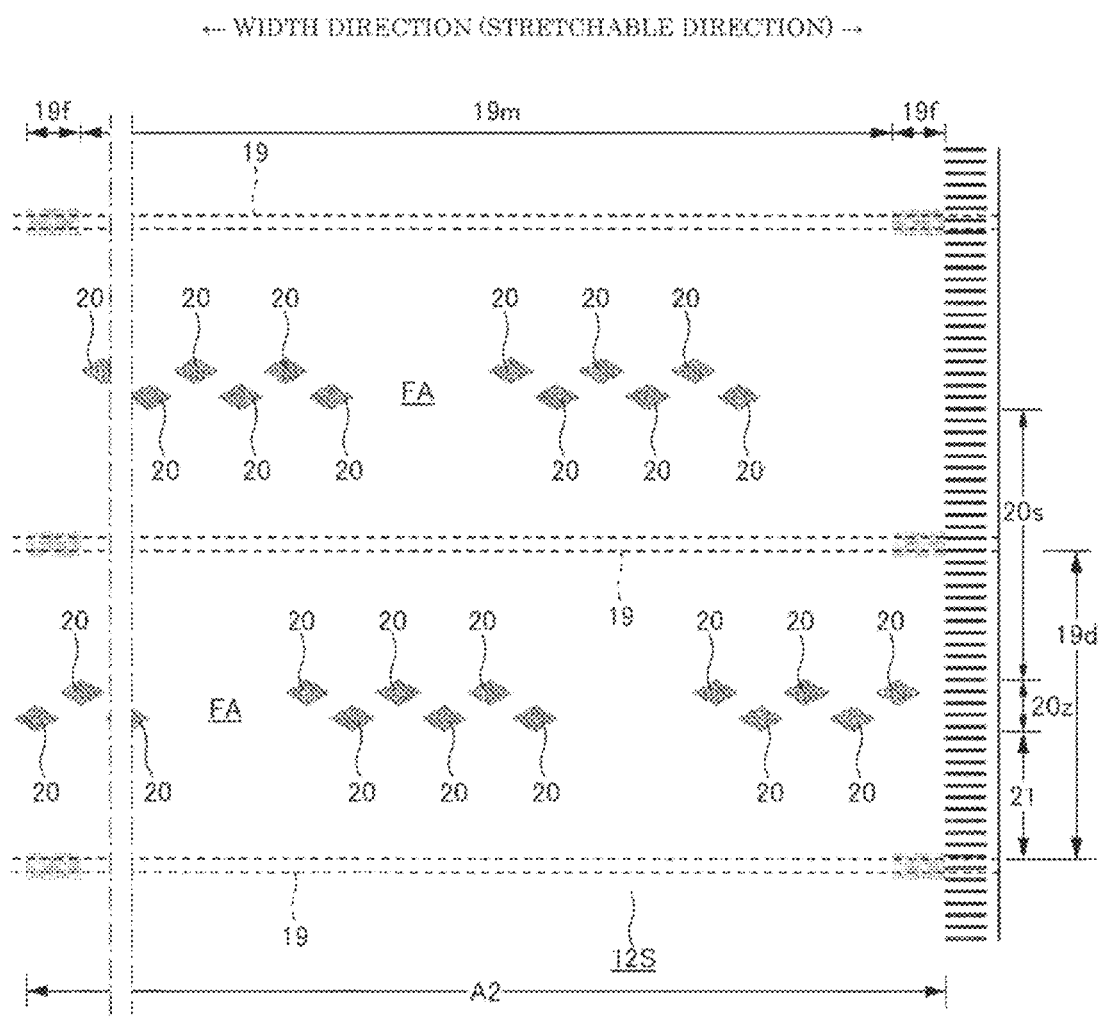
FIG. 23 is an enlarged plan view of essential components of the outer member in a spread state.

Examples of the configurations in which the sheet bonding sections 20 substantially continuously extend in the width direction include a configuration in which the sheet bonding sections 20 continuously extend in the width direction (the two sheet layers 12S and 12H are bonded at continuous lines in the width direction) as illustrated in FIGS. 11 and 12; a configuration in which the sheet bonding sections 20 are disposed intermittently in the width direction (the two sheet layers 12S and 12H are intermittently bonded in the width direction) but a partial or entire group of the multiple sheet bonding sections 20 disposed in a single inter-free region FA is continuous (without interruption) along the front-back direction as illustrated in FIGS. 13, 14, 21, and 22; and a configuration in which a partial or entire group of the multiple sheet bonding sections 20 disposed in two adjacent inter-free regions FA in the front-back direction is continuous (without interruption) along the front-back direction as illustrated in FIG. 23.

The sheet bonding sections 20 may be completely continuous in the stretchable direction, but in such a case, a reduction in softness is inevitable. Fusion of the sheet layers composed of non-woven fabric or the like at the sheet bonding sections 20 in the form of continuous lines causes ready tearing of the sheets along the sheet bonding sections 20. Thus, it is preferred to intermittently dispose the sheet bonding sections 20 along the stretchable direction.

Configurations in which the sheet bonding sections 20 are intermittently disposed but is substantially continuous along the width direction include a single-array configuration in which the sheet bonding sections 20 align at predetermined intervals in a single array along the stretchable direction as illustrated in FIG. 13; and a multi-array configuration in which multiple arrays of sheet bonding sections 20 are disposed in the front-back direction, and the sheet bonding sections 20 in each array are disposed in a staggered pattern such that they overlap with the sheet bonding sections 20 in the other arrays adjacent in the front-back direction as illustrated in FIGS. 14 and 19 to 21. It is preferred to intermittently dispose the sheet bonding sections 20 in the width direction in this way because softness is less likely to decrease. The individual sheet bonding sections 20 in the multi-array configuration are smaller than those in the single-array configuration, and thus the softness is more enhanced in the multi-array configuration. Moreover, the two sheet layers 12S and 12H bonded at multiple sheet bonding sections 20 have a sufficient bonding strength. As illustrated in FIG. 23, the groups of sheet bonding sections 20 in the respective inter-free regions FA do not appear substantially continuous in the width direction in the individual groups but appear substantially continuous in the width direction when multiple groups of the sheet bonding sections 20 in the inter-free regions FA adjacent to each other in the front-back direction are collectively viewed. This configuration achieves the most enhanced softness.

In the single-array configuration, it is preferred that the width-direction overlapping width 20w of a first sheet bonding section 20 and a second adjacent sheet bonding section 20 in the stretchable direction be larger than the front-back interval 20d (the maximum value is selected, if the interval varies) of the first sheet bonding section 20 and the second sheet bonding section 20 in the overlapping area. In the multi-array configuration, it is preferred that the width-direction overlapping width of a first sheet bonding section 20 in an array and a second sheet bonding section 20 in another array adjacent in the front-back direction be larger than the front-back interval of these sheet bonding sections 20.

In the multi-array configuration, in particular, it is preferred that the sheet bonding sections 20 in the respective arrays be disposed such that portions of the sheet bonding sections 20 in the front-back direction in the respective arrays and portions of the sheet bonding sections 20 in the front-back direction in adjacent arrays overlap in the front-back direction, as illustrated in FIG. 14.

The individual sheet bonding sections 20 may have any appropriate shape, such as a circle, an ellipse, or a polygon (triangle, square, etc.). To simplify the shape of the sheet bonding sections 20 in a single-array configuration, triangles, parallelograms (as illustrated in the drawings), and combination thereof are preferred. To simplify the shape of the sheet bonding sections 20 in a multi-array configuration, triangles, diamonds, and combination thereof (as illustrated in the drawings) are preferred.

Figure 24:
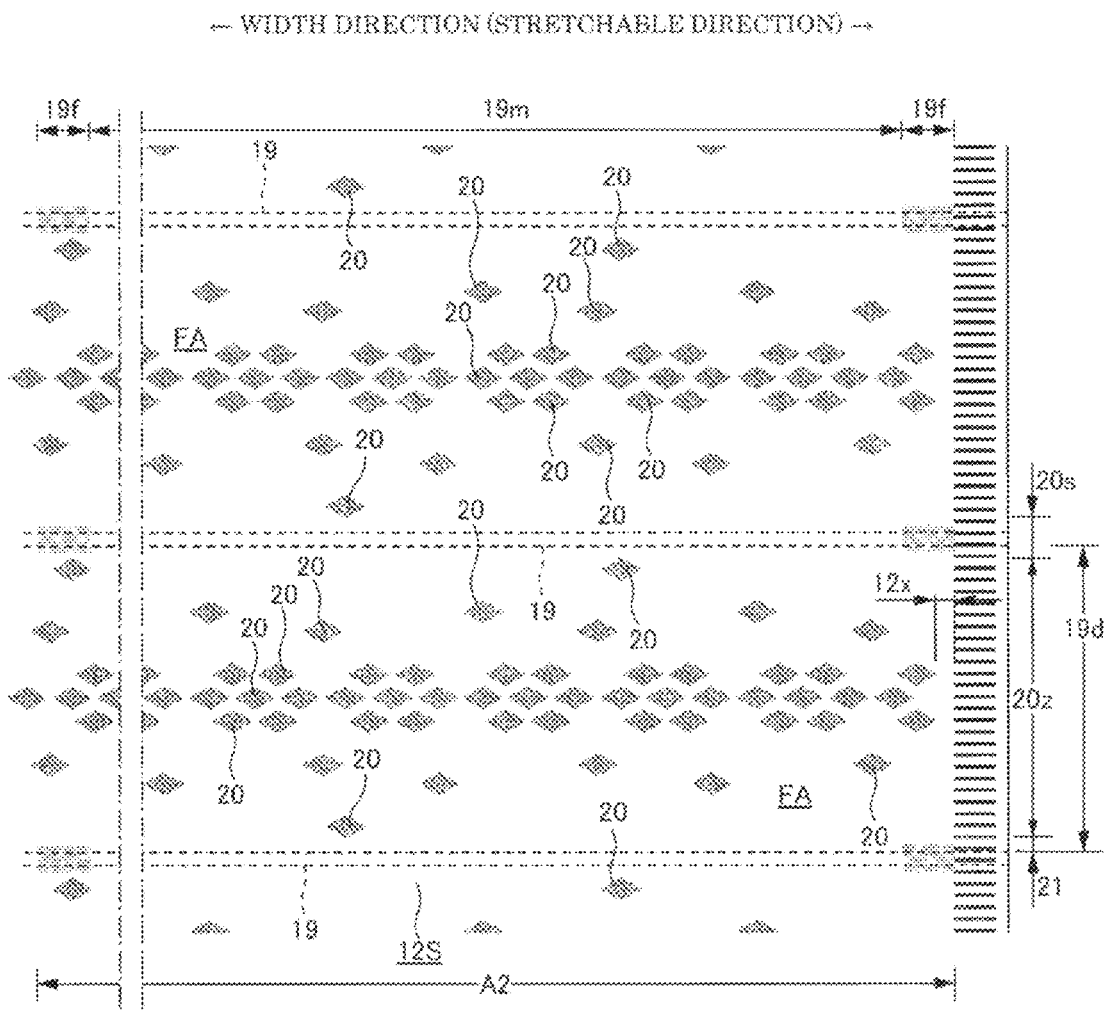
FIG. 24 is an enlarged plan view of essential components of the outer member in a spread state.
Figure 25:
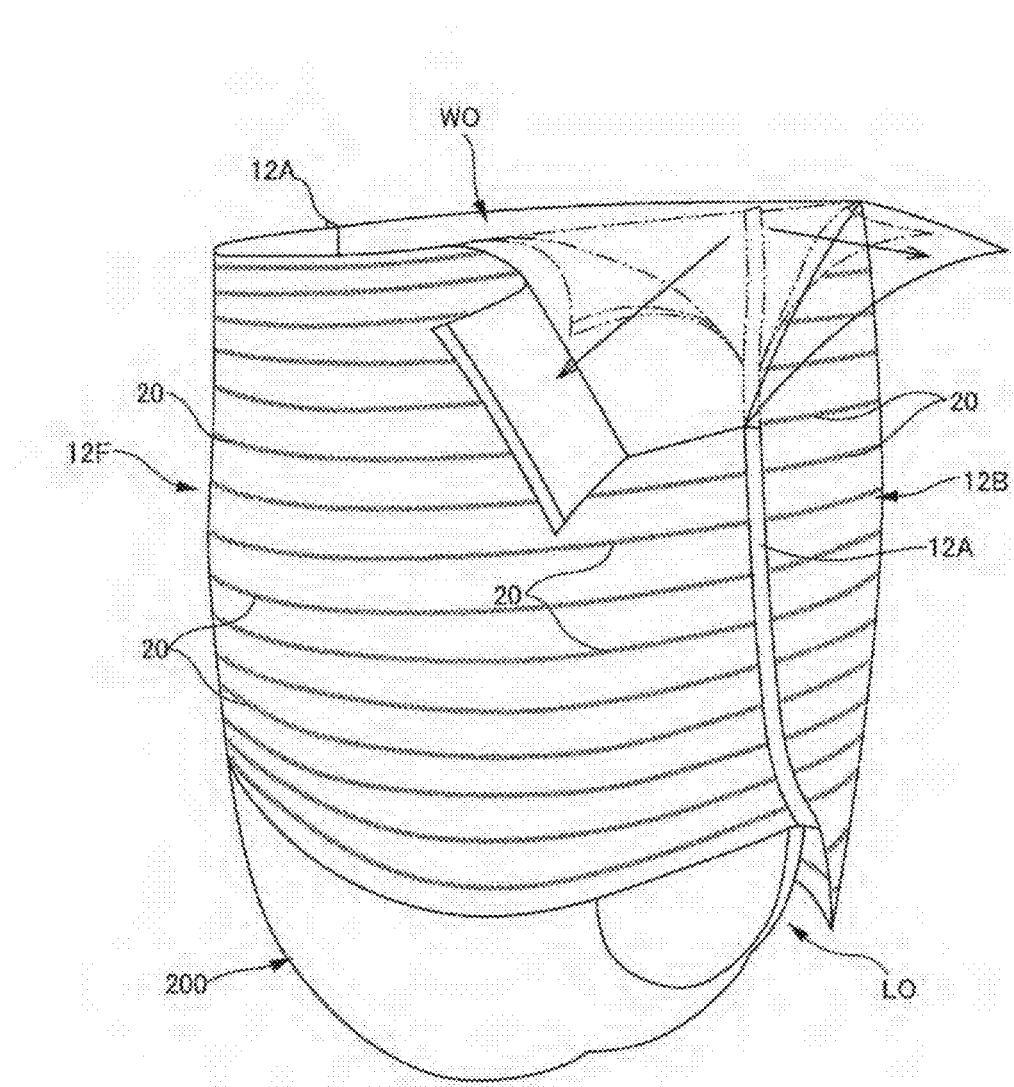
FIG. 25 is a perspective view of an underpants-type disposable diaper.

The sheet bonding sections 20 may have any appropriate dimensions and may be arrayed at any appropriate intervals. Sheet bonding sections 20 intermittently disposed preferably have the following dimensions and intervals:

Maximum length 20x of the sheet bonding sections in the width direction: 0.5 to 5.0 mm Maximum length 20y of the sheet bonding sections in the front-back direction: 0.2 to 2.0 mm Width-direction interval 20t of the sheet bonding sections: 0.1 to 0.9 times the maximum length 20x of the sheet bonding sections in the width direction Front-back interval 20d of the sheet bonding sections: 0.5 to 1.5 times the maximum length 20y of the sheet bonding sections in the front-back direction Width-direction overlapping width 20w of the sheet bonding sections: 0.2 time or more the front-back interval 20d of the sheet bonding sections Front-back length 20z of an area of the inter-free region including the sheet bonding sections: 1 to 10 mm Front-back interval 20s of the sheet bonding sections in an adjacent inter-free region: 4 to 20 mm Alternatively, the sheet bonding sections 20 may be intermittently arrayed (substantially discontinuous) in the width direction on view of a group of sheet bonding sections 20 in each inter-free regions FA or a group of sheet bonding sections 20 in an inter-free region FA adjacent to other inter-free region FA in the front-back direction, as illustrated in FIG. 24. In detail, the high overall unity of the two sheet layers 12S and 12H can be achieved even with this configuration by forming a sufficiently small area including discontinuous sheet bonding sections 20 in the width direction and sufficiently long areas including substantially continuous sheet bonding sections 20 and being adjacent to the sufficiently small area in the width direction. Thus, in the former area, the two sheet layers 12S and 12H deform to maintain continuity with the latter areas so that the two sheet layers 12S and 12H form a wave pattern while conforming to each other, as in the configuration illustrated in FIG. 16.

The two sheet layers 12S and 12H in the inter-free regions FA have an increased mobility toward the central area in the front-back direction. Thus, it is preferred to increase the area rate of the sheet bonding sections 20 to enhance the unity of the two sheet layers 12S and 12H because the conforming state of the two sheet layers 12S and 12H is barely distorted. At the edges of the inter-free regions FA in the front-back direction (i.e., in the vicinity of the elastically stretchable members 19), the elastically stretchable members 19 hinder the approximation of the two sheet layers 12S and 12H. Thus, for the sheet layers 12S and 12H to absorb the hindering effect of the elastically stretchable members 19 and independently deform (contract or bend) so that the sheet layers 12S and 12H conform with each other, it is preferred that the area rate of the sheet bonding sections 20 be small and the mobility of the sheet layers 12S and 12H to be high. Low mobility of the sheet layers 12S and 12H relative to the elastically stretchable members 19 causes the elastically stretchable members 19 and the sheet layers 12S and 12H to deform as an integrated body. Thus, the sheet layers 12S and 12H slightly separate from the elastically stretchable members 19 and form many small wrinkles, which generate a coarse unpleasant texture. Thus, a preferred configuration includes sheet bonding sections 20 arrayed such that the area rate of the sheet bonding sections 20 (the rate of the areas of the sheet bonding sections 20 per unit area) gradually decreases toward the two front-back edges of each inter-free region FA, as in the illustrated embodiments.

The area rate of the sheet bonding sections 20 can be varied toward the two front-back edges of each inter-free region FA by providing unbonded regions 21, as in the illustrated embodiments, and/or providing a smaller number of sheet bonding sections 20 in arrays closer to the front-back edges of the inter-free regions FA in a multi-array configuration. The shape and/or area of the individual sheet bonding sections 20 may be modified.

In a spread state of the intermittent stretchable regions A2 and A3, each inter-free region FA includes three portions FA1, FA2, and FA3 having equal widths in the front-back direction, where the central portion FA2 is positioned in the center of the portions FA1, FA2, and FA3 in the front-back direction and the side portions FA1 and FA3 are positioned adjacent to the central section FA2 (see FIG. 22). Usually, it is preferred that the area rate of the sheet bonding sections 20 to the central portions FA2 be within the range of 3% to 25%, preferably 5% to 20%, and the area rate of the sheet bonding sections 20 to the respective side portions FA1 and FA3 be 10% or less, preferably 3% or less. The rate of the area rate of the sheet bonding sections 20 to the central portions FA2 to the area rate of the sheet bonding sections 20 to the respective side portions FA1 and FA3 is 20% or less, preferably 10% or less. It is even more preferred that the side portions FA3 is free from the sheet bonding sections 20 because this increases not only the mobility of the sheet layers 12S and 12H relative to the elastically stretchable members 19 but also decreases the risk of the sheet bonding sections 20 coming into contact with the elastically stretchable members 19 during production (the risk of the elastically stretchable members 19 unintentionally being cut in the case of bonding by welding).

Other configurations may include a configuration in which the area rate of the sheet bonding sections 20 is constant across the inter-free regions FA in the front-back direction and a configuration in which the area rate of the sheet bonding sections 20 gradually increases toward the two front-back edges of each inter-free region FA.

The sheet bonding sections 20 and the fixed ends 19f of the elastically stretchable members 19 in the continuous stretchable regions A3 and the intermittent stretchable regions A2 may have any shape different from those according to the illustrated embodiments, for example, the shapes described in PTL 1. In such a case also, the sheet bonding sections 20 should be separated from the side seal portions 12A, as described above.

(Formation of Non-Stretchable Region)

The non-stretchable region A1 can be formed by disposing the elastically stretchable members 19 between the inner sheet layer 12H and the outer sheet layer 12S; fixing only the fixed ends 19f of the elastically stretchable members 19 with a hot-melt adhesive at the edge portions in areas to be defined as the intermittent stretchable regions A2; and then cutting each elastically stretchable member 19 at one or more intermediate positions in the width direction within the areas to be the non-stretchable region A1 through pressurization and heating, or snicking substantially all of the elastically stretchable members 15, 16, and 19 through pressurization and heating, so that the elasticity of the intermittent stretchable regions A2 is preserved while the elasticity of the non-stretchable region A1 is nullified.

FIG. 19(a) illustrates a case where the elastically stretchable members 19 are cut at one intermediate position in the width direction. The cutting is performed with a seal roll 70 having a circumferential surface provided with press segments 71 each including a cutting convex 72 disposed at a given position on the circumference and heated to a predetermined temperature; and an anvil roll 80 having a smooth surface and facing the seal roll 70. The target to be cut, which includes the inner sheet layer 12H, the outer sheet layer 12S, and the elastically stretchable members 19 disposed therebetween, is disposed between the rolls 70 and 80, and only the elastically stretchable members 19 in the portions nipped between the cutting convexes 72 and the circumferential surface of the anvil roll 80 are cut through pressurization and heating. In a product processed in this way, each non-stretchable region A1 includes residual elastically stretchable members 18 containing only the residual pieces continuing from the elastically stretchable members 19 in the intermittent stretchable regions A2, and one melted mark 22 or cutting mark between the outer sheet layer 12S and the inner sheet layer 12H, as illustrated in FIGS. 20(a) and 20(b). Although not illustrated, in the case of cutting at multiple positions, a seal roll 70 having multiple cutting convexes 72 along the circumference may be used.

FIG. 19(b) illustrates a case where the elastically stretchable members 19 are substantially entirely snicked. The snicking is performed with a seal roll 70 having a circumferential surface provided with press segments 71 each including multiple cutting convexes 73 intermittently disposed in a staggered pattern and heated to a predetermined temperature and an anvil roll 80 having a smooth surface facing the seal roll 70. The target to be cut, which includes the inner sheet layer 12H, the outer sheet layer 12S, and the elastically stretchable members 15, 16, 17 and 19 disposed therebetween, is disposed between the rolls 70 and 80, and only the elastically stretchable members 19 in the portions nipped between the cutting convexes 73 and the circumferential surface of the anvil roll 80 are cut through pressurization and heating. In a product processed this way, the non-stretchable region A1 includes residual elastically stretchable members 18 intermittent in the front-back and width directions containing residual pieces continuing from the elastically stretchable members 19 in the stretchable regions A2 and cut pieces of the elastically stretchable members discontinued from the elastically stretchable members 19 in the intermittent stretchable regions A2, between the outer sheet layer 12S and the inner sheet layer 12H; and melted marks 22 or cutting marks, as illustrated in FIG. 20(c).

(Sheet Bonding Sections in Non-Stretchable Regions)

Figure 6:
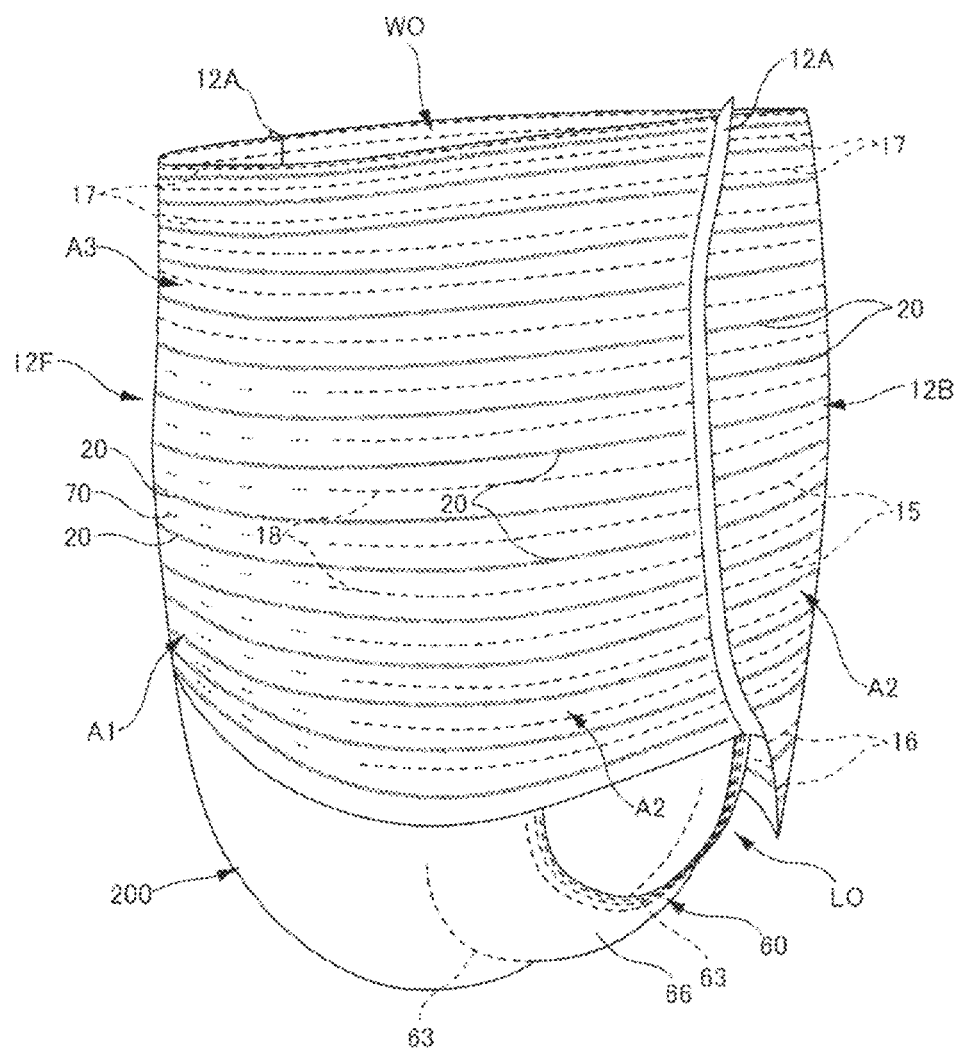
FIG. 6 is a perspective view of an underpants-type disposable diaper.

Although the sheet bonding sections 20 may be omitted in the non-stretchable region A1, the sheet bonding sections 20 should preferably be provided to prevent the outer sheet layer 12S from being undesirably displaced or separated from the inner sheet layer 12H. The sheet bonding sections 20 in the non-stretchable region may be of any type as long as the two sheet layers 12S and 12H are bonded. In the non-stretchable region A1, as illustrated in FIGS. 2, 6, and 20, it is preferred that the residual elastically stretchable members 70 be unfixed to the two sheet layers 12S and 12H and the two sheet layers 12S and 12H be bonded at the sheet bonding sections 20 substantially continuous in the width direction at the two edges of the residual elastically stretchable members 70 in the front-back direction. The residual elastically stretchable members 70 unfixed to the two sheet layers 12S and 12H in this way can completely cancel out the contraction force of the residual elastically stretchable members 70 applied to the two sheet layers 12S and 12H. In the non-stretchable region A1, the sheet bonding sections 20 substantially continuous in the width direction bond the two sheet layers 12S and 12H at the two edges of the residual elastically stretchable members 70 in the front-back direction. Thus, a shift of the residual elastically stretchable members 70 in the front-back direction is limited to the area between adjacent sheet bonding sections 20 on the two edges of the residual elastically stretchable members 70 in the front-back direction. This prevents a large shift that impairs the pleasing appearance. In the non-stretchable region A1, the residual elastically stretchable members 70 may be fixed to the two sheet layers 12S and 12H with a hot-melt adhesive. In the case where the elastically stretchable members 19 are cut at one or more intermediate positions in the width direction, as illustrated in FIGS. 20(a) and 20(b), the volume of the hot-melt adhesive to be applied should be adjusted so as to reduce the adhesive force. In the case where the elastically stretchable members 19 are snicked, as illustrated in FIG. 20(c), the elasticity of the non-stretchable region A1 can be substantially nullified even with a large adhesive force.

The sheet bonding sections 20 in the non-stretchable region A1 may be basically the same as the sheet bonding sections 20 in the intermittent stretchable regions A2. Alternatively, the sheet bonding sections 20 in the non-stretchable region A1 may be different in shape, dimension, number, and position from the sheet bonding sections 20 in the intermittent stretchable regions A2. For example, multiple arrays of the sheet bonding sections 20, such as those illustrated in FIG. 13, may be disposed in the non-stretchable region A1 between the residual elastically stretchable members 70, and the distance between the residual elastically stretchable members 70 and the sheet bonding sections 20 may be narrowed to effectively prevent the shift of the residual elastically stretchable members 70. At the same time, a single array of the sheet bonding section 20 may be disposed in each intermittent stretchable region A2 between adjacent elastically stretchable members 19, as illustrated in FIG. 11, in strong consideration of the softness of the intermittent stretchable regions A2.

In view of ready and stable production, it is preferred that the sheet bonding sections 20 in the non-stretchable region A1 be identical in shape, dimension, number, and position to the sheet bonding sections 20 in the intermittent stretchable regions A2, as illustrated in FIGS. 2, 6, and 20. It is preferred that at least the sheet bonding sections 20 in the intermittent stretchable regions A2 and the sheet bonding sections 20 in the non-stretchable region A1 be substantially continuous in the width direction.

In such a case, the spaces between the two sheet layers 12S and 12H in the intermittent stretchable regions A2 are in communication with the space between the two sheet layers 12S and 12H in the non-stretchable region A1. This may cause the residual elastically stretchable members 70 in the non-stretchable region A1 to shift into the space in the intermittent stretchable regions A2. Thus, as illustrated in FIGS. 1 and 14, it is also preferred to form the fixed ends 19f of the elastically stretchable members 19 at least at the inner edges of the intermittent stretchable regions A2 in the width direction with a hot-melt adhesive continuing across the entire front-back direction of the intermittent stretchable regions A2, and to simultaneously bond the two sheet layers 12S and 12H over the entire front-back direction of the intermittent stretchable regions A2. In this way, the space between the two sheet layers 12S and 12H in the non-stretchable region A1 is sealed at the edges of the non-stretchable region A1 in the width direction, thereby preventing impairment of the pleasing appearance due to a shift of the residual elastically stretchable members 70 into the intermittent stretchable regions A2.

Other details of the substantially continuous sheet bonding sections 20 in the non-stretchable region A1 are omitted here because they have already been described in the section on the sheet bonding sections 20 in the stretchable regions.

(Inner Member)

The inner member 200 may have any shape and structure. For example, the inner member 200 may have the following shape and structure. The inner member 200 may have any shape. In this embodiment, the inner member 200 has a rectangular shape. The inner member 200 includes a liquid pervious top sheet 30 adjacent to the skin of the wearer, a liquid impervious sheet 11, and an absorbent element 50 disposed therebetween, as illustrated in FIGS. 3 to 5. The inner member 200 is the main section that provides an absorbing function. Reference sign 40 represents an intermediate sheet (also referred to as a second sheet) disposed between the top sheet 30 and the absorbent element 50 for quick transportation of the liquid passing through the top sheet 30 into the absorbent element 50, and reference sign 60 represents leg-surrounding gathers 60 that extend along the edges of the absorbing face of the inner member in the width direction and erect around the legs of the wearer, to prevent leakage of excretion from the two edges of the inner member 200.

(Top Sheet)

The top sheet 30 may be composed of any liquid pervious materials, such as porous or non-porous non-woven fabric and a porous plastic sheet. In a case where the top sheet 30 also functions as a covering material of liquid impervious sheets 64 of the leg-surrounding gathers 60, as illustrated in FIGS. 3 and 4, the top sheet 30 is composed of non-woven fabric. There is no particular limitation on the kind of raw fiber for the non-woven fabric. Examples of such raw fiber include synthetic fibers based on olefin, such as polyethylene and polypropylene, polyester, and polyimide, reproduced fibers, such as rayon and cupra; natural fibers, such as cotton; and mixed fibers and composite fibers composed of two or more of these fibers. The non-woven fabric may be produced through any process. Examples of known processes include spunlacing, spunbonding thermal bonding, melt blowing, needle punching, air through bonding, and point bonding. For example, spunbonding and spunlacing are suitable for achieving softness and draping, whereas air through bonding, point bonding, and thermal bonding are suitable for bulkiness and softness.

The top sheet 30 may be composed of a single sheet or a layered sheet formed by sticking two or more sheets to each other. Similarly, the top sheet 30 may be composed of a single sheet or two or more sheets in a planar direction.

Figure 7:
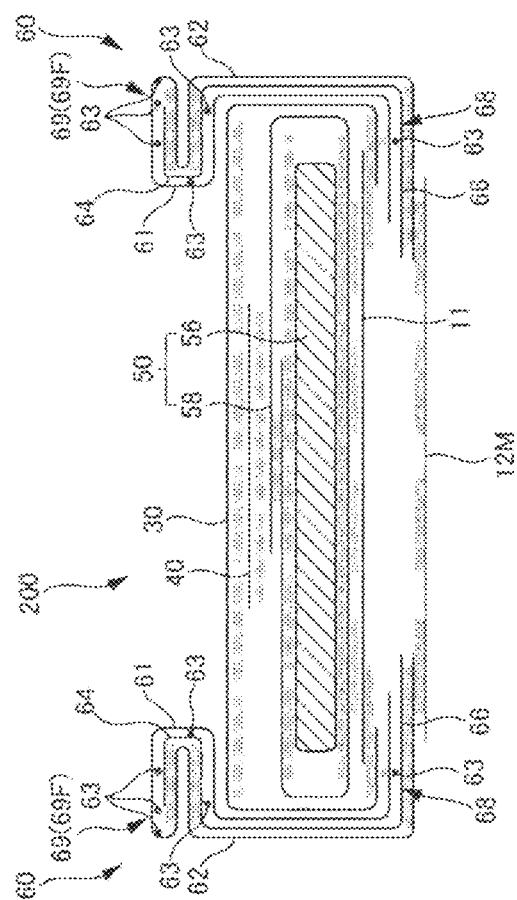
FIG. 7 is a cross-sectional view of an inner member taken along line 3-3 in FIG. 1.
Figure 8:
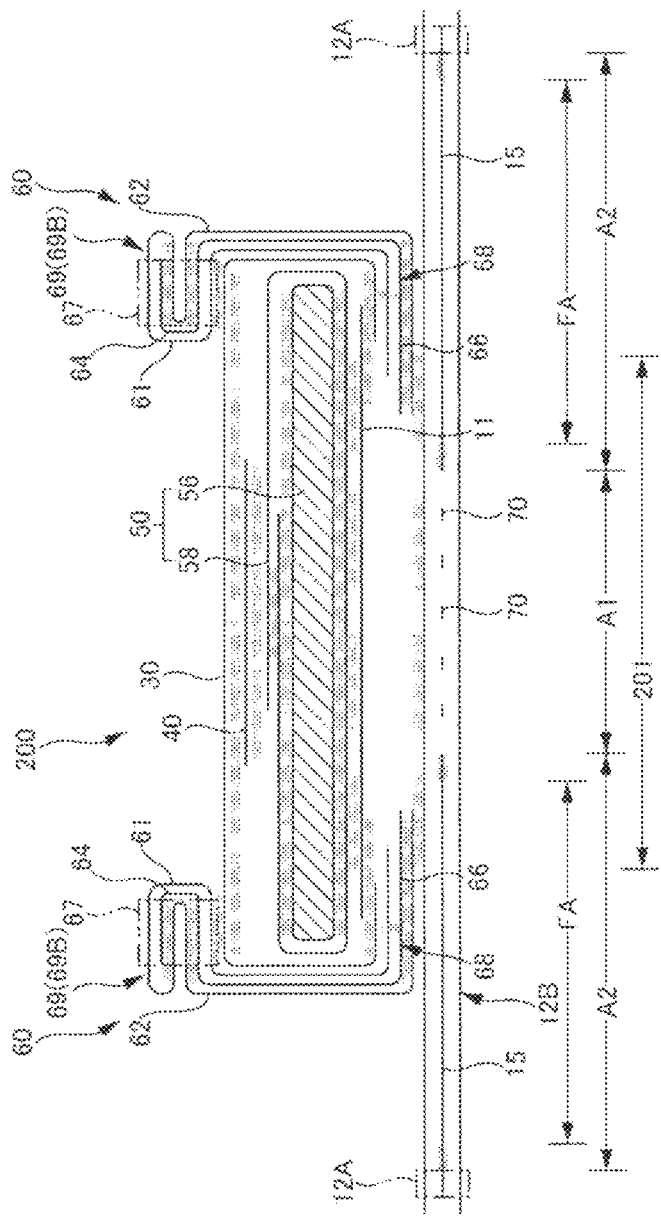
FIG. 8 is a cross-sectional view of the inner member taken along line 4-4 in FIG. 1.

If the two edges of the top sheet 30 in the width direction do not function as the covering material of the liquid impervious sheets 64 of the leg-surrounding gathers 60, the top sheet 30 can be passed between the absorbent element 50 and the leg-surrounding gathers 60 to the back surface side of the absorbent element 50 and bonded to the liquid impervious sheet 11 and the leg-surrounding gathers 60 with a hot-melt adhesive to prevent permeation of liquid, as illustrated in FIGS. 7 and 8.

(Intermediate Sheet)

With reference to FIGS. 7 and 8, an intermediate sheet (which is also referred to as "second sheet") 40 having hydrophilicity higher than that of the top sheet may be disposed on the back face of the top sheet 30. The intermediate sheet 40 prevents returning of liquid absorbed by the absorber and establishes a dry texture of the surface of the top sheet 30. The intermediate sheet 40 may be omitted.

Examples of materials for the intermediate sheet 40 include the same materials for the top sheet 30, spunlace fabric, spunbond fabric, SMS, pulp non-woven fabric, a sheet composed of a mixture of pulp and rayon, pointbond fabric, and crepe paper. Air-through non-woven fabric is particularly preferred for its bulkiness. Air-through non-woven fabric is preferably composed of composite fibers having a core-in-sheath structure. In such a case, the core is composed of a resin, such as polypropylene (PP), preferably polyester (PET) having high stiffness. The basis weight is preferably within the range of 20 to 80 g/m$^2$, more preferably 25 to 60 g/m$^2$. The fineness of the raw fibers of the non-woven fabric is preferably within the range of 2.2 to 10 dtex. For the bulkiness of the non-woven fabric, it is preferred that all or some of the raw fibers be mixed fibers, such as offset-core fibers having an eccentric core, hollow fibers, or hollow off-set core fibers.

The intermediate sheet 40 according to the illustrated embodiments has a width smaller than that of the absorber 56 and is disposed in the central area. Alternatively, the intermediate sheet 40 may be disposed over the maximum width. The intermediate sheet 40 may have a longitudinal length the same as that of the absorber 56 or may have a small length centered on the section receiving liquid.

(Liquid impervious Sheet)

The liquid impervious sheet 11 disposed on the back face of the absorber 56 may be composed of any material. Examples include plastic films composed of olefin resin, such as polyethylene and polypropylene. It is preferred that the liquid impervious sheet 11 be composed of a material having liquid imperviousness and moisture permeability, which is nowadays preferred in view of prevention of stuffiness. An example of a common plastic film having moisture permeability as a macroporous plastic film produced through kneading an olefin resin, such as a polyethylene resin or a polypropylene resin, and an inorganic filler, forming a sheet with the kneaded materials, and monoaxilly or biaxially stretching the sheet.

The liquid impervious sheet 11 may extend further laterally than the absorber 56 and also function as the liquid pervious film 64 in the leg-surrounding gathers 60, as illustrated in FIGS. 3 and 4. Alternatively, the liquid impervious sheet 11 may have a width smaller than that of the back face of the absorbent element 50, as illustrated in FIGS. 7 and 8, or extend along the two side faces of the absorbent element 50 in the width direction to reach the edges of the faces of the absorbent element 50 adjacent to the top sheet 30.

The inner face of the liquid impervious sheet 11, in particular the face adjacent to the absorber 56 may be provided with an excretion indicator that changes color in response to absorption of liquid.

(Absorbent Element)

The absorbent element 50 includes an absorber 56 and a wrapping sheet 58 covering the entire absorber 56. The wrapping sheet 58 may be omitted.

(Absorber)

The absorber 56 may be composed of a fiber assembly. Examples of the fiber assembly include fluff pulp, an assembly of short fibers, such as synthetic fibers, assembled through fiber stacking, and an assembly of filaments acquired through opening tows (fiber bundles) of synthetic fibers, such as cellulose acetate, as required. The fiber basis weight of fluff pulp or stacked short fibers may be within the range of approximately 100 to 300 g/m$^2$, and the fiber basis weight of a filament assembly may be within the range of approximately 30 to 120 g/m$^2$, for example. The fineness of synthetic fiber is within the range of 1 to 16 dtex, preferably 1 to 10 dtex, more preferably 1 to 5 dtex. Although the filaments in a filament assembly may be composed of non-crimped fiber, it should preferably be crimped fiber. The degree of crimp of crimped fiber is, for example, within the range of 5 to 75 per inch, preferably 10 to 50 per inch, more preferably 15 to 50 per inch. Uniformly crimped fiber is often used. It is preferred that high absorbent polymer particles be dispersed in the absorber 56.

The absorber 56 may have a rectangular shape. It is preferred that the absorber 56 be disposed on and between the front end portion and the back end portion and have a shape similar to the outline of an hourglass in which the curved portion has a width smaller than that of the front end portion and the back end portion, as illustrated in FIG. 6, because the fit of the absorber 56 and the leg-surrounding gathers 60 to the legs is enhanced.

The absorber may have any appropriate dimensions. It is preferred that the absorber extends in the front-back and width directions to the peripheral edges of the inner member or the vicinity thereof. Reference sign 56X represents the width of the absorber 56.

(High Absorbent Polymer Particles)

The absorber 56 may partially or entirely contain high absorbent polymer particles. High absorbent polymer particles include "powder" in addition to "particles." The high absorbent particles 54 may be those used for similar types of absorbent articles. Preferred examples of such particles include particles of 30 weight % or less remaining on a standard 500-μm sieve (JIS Z8801-1:2006) after sifting (shook for five minutes) or particles of 60 weight % or more remaining on a standard 180-μm sieve (JIS Z8801-1:2006) after sifting (shook for five minutes).

There is no particular limitation on the material for the superabsorbent polymer particles. Preferably, the material has water absorption capacity (JIS K7223-1996 "Testing Method for Water Absorption Capacity of Super Absorbent Polymers") of 40 g/g or more. Examples of the superabsorbent polymer particles are based on starch, cellulose, and synthetic polymer, such as graft copolymer of starch and acrylic acid (salt), saponified copolymers of starch and polyacrylonitrile, cross-linked sodium carboxymethyl cellulose, and acrylic acid (salt) copolymer. Preferably, the superabsorbent polymer particles are in the form of generally used particulate. Alternatively, the high absorbent polymer particles may have another form.

The high absorbent polymer particles have a water absorption rate of 70 second or less, preferably 40 seconds or less. A water absorption rate too small causes ready returning of the liquid in the absorber 56 to the outside of the absorber 56.

The basis weight of the superabsorbent polymer particles can be appropriately determined in accordance with the required absorption volume of the absorber 56 depending on use. Although the basis weight depends on the use, it may be within the range of 50 to 350 g/m². A basis weight of polymers of less than 50 g/m² fails to achieve a sufficient absorption volume. A basis weight of polymers of more than 350 g/m² saturates the absorption volume.

The density or volume of the high absorbent polymer particles dispersed in the absorber 56 may be adjusted in the planer direction, as required. For example, the volume of the particles at the liquid excretion site may be higher than the volume at the other sites. In consideration of the difference between male and female physiology, the density or volume can be increased in the front portion in diapers for male and the density or volume can be increased in the central portion in diapers for female. Alternatively, sections free from polymers may be provided locally (in spots, for example) in the planar direction of the absorber 56.

(Wrapping Sheet)

Examples of the material for the wrapping sheet 58 include liquid pervious materials, such as tissue paper, crepe paper, non-woven fabric, polyethylene laminated non-woven fabric, and a porous sheet. Preferably, the highly absorbent polymer particles do not pass through the sheet. In the case where non-woven fabric is used in place of crepe paper, hydrophilic SMS (SMS, SSMMS or the like) non-woven fabric is preferred. Examples of such materials include polypropylene and polyethylene/polypropylene composite. The basis weight is within the range of 5 to 20 g/m², preferably 8 to 15 g/m².

The wrapping sheet 58 may have any appropriate configuration. In view of ready production and prevention of leakage of high absorbent polymer particles from the front-back edges, it is preferred that the wrapping sheet 58 be cylindrically wound around the front and back faces and the two edges of the absorber 56, the front-back edges of the wrapping sheet 58 respectively protrude from the front and back of the absorber 56, and the protrusion be compressed in the thickness direction and bonded with a bonding means, such as a hot-melt adhesive.

(Leg-Surrounding Gathers)

The leg-surrounding gathers 60 extend along the two edges of the absorbing face of the inner member 200 in the width direction and erect toward the legs of the wearer, to prevent side leakage of urine or loose stool due to lateral migration of the urine or loose stool along the top sheet 30.

With reference to FIGS. 3 and 4, the leg-surrounding gathers 60 of this embodiment each includes inner non-woven fabric layers 61 constituting the inner face in the width direction; an outer non-woven fabric layer 62 constituting the outer face in the width direction; elastically stretchable gather members 63 disposed between the inner non-woven fabric layer 61 and the outer non-woven fabric layer 62 along the front-back direction at least at the distal edge of the intermediate portion in the front-back direction; and a liquid impervious sheet 64 (11) disposed between the inner non-woven fabric layer 61 and the outer non-woven fabric layer 62 across an area between the proximal edge and a position closer to the distal edge than the proximal edge. In the illustrated embodiments, fabric-free sections 65 are defined as sections of the leg-surrounding gathers 60 including the liquid impervious sheet 64 in respective areas between the distal edges and the proximal edges, extending entirely over the leg-surrounding gathers 60 in the front-back direction, free from the inner non-woven fabric layers 61, and exposing the liquid impervious sheet 64. The fabric-free sections 65 free from the inner non-woven fabric layers 61 in the leg-surrounding gathers 60 can reduce the volume of non-woven fabric to be used. The distal edges of the leg-surrounding gathers 60 come into contact with the skin of the wearer. The fabric-free sections 65 disposed remote from the distal edges prevent the liquid impervious sheet 64 from coming into contact with the skin of the wearer, thereby preventing deterioration of the texture.

The entire liquid impervious sheet 64 may be covered with the inner non-woven fabric layers 61 extending to the edges of the top sheet 30, in the embodiment illustrated in FIGS. 1 to 6, or the leg-surrounding gathers 60 having the structure illustrated in FIG. 7 or 8.

The elastically stretchable gather members 63 may be disposed only at the distal edges of the respective leg-surrounding gathers 60. It is preferred that multiple elastically stretchable gather members 63 be disposed between the distal edges and the proximal edges of the respective leg-surrounding gathers 60 at predetermined intervals, as in the illustrated embodiments. Usually, the number of elastically stretchable gather members 63 is preferably within the range of 2 to 6, and the intervals 60d thereof are preferably within the range of 3 to 10 mm. The multiple elastically stretchable gather member 63 disposed at the predetermined intervals in this way causes the sections corresponding to the intervals of the elastically stretchable gather member 63 to externally curve. Thus, it is preferred that the fabric-free sections 65 only be provided in these sections, as in the illustrated embodiments, because the liquid impervious sheet 64 exposed in the fabric-free sections 65 is depressed and barely comes into contact with the skin of the wearer. In this case, with reference to FIGS. 1 to 6, it is preferred that at least one elastically stretchable gather member 63 be respectively disposed at least only at the distal edge and the proximal edge of each leg-surrounding gather 60 at predetermined intervals, and the fabric-free sections 65 be disposed only in the sections corresponding to the intervals between the elastically stretchable gather member 63 disposed at the proximal edge and the elastically stretchable gather member 63 disposed at the distal edge.

The front-back areas of the leg-surrounding gathers 60 in which the elastically stretchable gather members 63 are disposed may extend over the entire front-back direction of the leg-surrounding gathers 60. It is preferred that the front-back areas be smaller than front-back areas of the erected areas of the leg-surrounding gathers 60.

The elastically stretchable gather members 63 may be disposed on either the inner side of the liquid impervious sheet 64 disposed inside the leg-surrounding gathers 60, as illustrated in FIGS. 3 and 7, or the outer side of the liquid impervious sheet 64 (not shown), with the proviso that the elastically stretchable gather members 63 are disposed between the inner non-woven fabric layer 61 and the outer non-woven fabric layer 62 (thus, not disposed in the fabric-free sections 65).

Each edge of the liquid pervious film 64 can be disposed anywhere between the proximal and distal edges of the corresponding leg-surrounding gather 60, for example, in an area between the proximal edge and an intermediate position between the proximal and distal edges. It is preferred that each edge of the liquid impervious sheet 64 be aligned with the corresponding distal edge to achieve sufficient imperviousness. In particular, it is preferred that each edge of the liquid pervious film 64 be disposed slightly remote from the corresponding distal edge (for example, by several elastically stretchable gather members, approximately 5 to 30 mm, in specific), as illustrated in FIGS. 3 and 4, so that the liquid impervious sheet 64 does not reach inside of the distal edges to maintain softness.

In the configuration in which the liquid impervious sheet 64 is exposed at the fabric-free sections 65, the liquid impervious sheet 64 exposed at the fabric-free sections 65 may urge against the skin of the wearer in the regions 60W of the leg-surrounding gathers 60 where the front outer member 12F and the back outer member 12B overlap. With reference to FIGS. 1 to 6, the regions 60W can be fixed to the front outer member 12F and the back outer member 12B and be contracted in the width direction by the elastically stretchable members 15 and 19 of the front outer member 12F and the back outer member 12B. In this way, even if the liquid impervious sheet 64 is exposed, the contact area with the skin in the regions 60W is significantly reduced by the contracted wrinkles, thereby reducing the influence on the texture. Sections of the leg-surrounding gathers 60 according to this embodiment disposed between the regions 60W fixed to the front outer member 12F and the back outer member 12B erect toward the legs of the wearer from the proximal edges adjacent to the absorber 56 in response to contraction of the elastically stretchable gather members 63, as indicated by the dash-double dot lines in FIG. 3.

The leg-surrounding gathers 60 may have any known structure. With reference to FIGS. 1 to 6, the top sheet 30 is composed of non-woven fabric, and the two edges thereof in the width direction extend across the side edges of the absorber 56; a gather sheet 66 composed of a non-woven fabric is disposed on the back face of the absorber 56, the two edges thereof in the width direction extending across the side edges of the absorber 56, the side edges of the gather sheet 66 being folded back; the distal edges of the folded portions 66r are separated from the distal edges of the top sheet 30; and the liquid impervious sheet 64 is disposed at least between the two folded portions 66r of the leg-surrounding gathers 60 and between the top sheet 30 and the gather sheet 66. As a result, the portion of the gather sheet 66 other than the folded portions 66r constitute the outer non-woven fabric layer 62; the folded portions 66r of the gather sheet 66 and the portions of the top sheet 30 extending laterally from the absorber 56 constitute the inner non-woven fabric layers 61; and the gaps between the folded portions 66r of the gather sheet 66 and the top sheet 30 constitute the fabric-free sections 65. As described above, portions of the inner non-woven fabric layer 61 closer to the proximal edges of the leg-surrounding gathers 60 relative to the fabric-free sections 65 are formed of the top sheet 30 and the other portions are formed of the gather sheet 66. In this way, the fabric-free sections 65 can be provided without cutting of the material, thereby achieving a significantly simple structure that can be readily produced.

In such a case, it is preferred that the liquid impervious sheet 64 of the leg-surrounding gathers 60 extend from one of the leg-surrounding gathers 60 to the other leg-surrounding gather 60 across the back face of the absorber 56, as illustrated in FIGS. 3 and 4, to achieve uniform imperviousness in not only the leg-surrounding gathers 60 but also on the back face of the absorber 56. Alternatively, the liquid pervious film 64 disposed inside the leg-surrounding gathers 60 and the liquid pervious film 11 covering the back face of the absorber 56 may be provided separately, as illustrated in FIGS. 7 and 8. In the latter case, the material for the liquid pervious film 64 disposed inside the leg-surrounding gathers 60 and the material for the liquid pervious film material 11 covering the back face of the absorber 56 may either be the same or different.

Similarly, it is preferred that the gather sheet 66 also be composed of a single sheet extending from one of the leg-surrounding gathers 60 to the other leg-surrounding gather 60 across the back face of the absorber 56, as illustrated in FIGS. 3 and 4, because a fabric-like external face can be produced without a separate crotch cover sheet described above. Alternatively, the gather sheet 66 and a crotch cover sheet 12M may be provided separately, as illustrated in FIGS. 7 and 8.

Another structure of the leg-surrounding gathers 60, such as that illustrated in FIGS. 7 and 8, may include attachment portions 68 that are fixed to the back face of the inner member 200; extending portions 69 that extend from the respective attachment portions 68 to the periphery of the front face of the inner member 200 along the edges of the inner member 200; fallen portions 69B in which the front-back edges of the respective extending portions 69 are fixed to the periphery of the front face of the inner member 200 in a fallen state; free portions 69F in which the intermediate region between the fallen portions in the extending portions are unfixed; and elastically stretchable gather members 63 that are fixed at least along the distal edges of the free portions 69F in the front-back direction in a stretched state. The free portions 69F of the respective leg-surrounding gathers 60 erect toward the respective legs of the wearer from the borders of the respective attachment portions 68 in response to contraction of the elastically stretchable gather members 63.

The extending portions 69 of the respective leg-surrounding gathers 60 illustrated in FIGS. 7 and 8 have proximal sections adjacent to the center in the width direction and distal sections folded back outward in the width direction from the distal edges of the proximal sections. Alternatively, the extending portions 69 may only have sections that are not folded back outward in the width direction and extend toward the center in the width direction (not shown).

In the front-back intermediate regions of the leg-surrounding gathers 60, which are to be erected, the inner non-woven fabric layer 61 and the outer non-woven fabric layer 62 can be bonded and the elastically stretchable gather members 63 can be fixed between the fabric layers 61 and 62, with at least one of the hot-melt adhesive through various application methods and a fixing means, such as heat sealing or ultrasonic sealing, through welding of the materials. It is preferred that the portions other than the bonded portions of the elastically stretchable gather members 63 not be bonded or be weakly bonded because bonding of the entire faces of the inner non-woven fabric layer 61 and the outer non-woven fabric layer 62 impairs softness. In the illustrated embodiments, the elastically stretchable gather members 63 are disposed between the inner non-woven fabric layer 61 and the outer non-woven fabric layer 62 after applying a hot-melt adhesive only to the circumferential surfaces of the elastically stretchable gather members 63 with an application means, such as a comb gun or a Surewrap nozzle. In this way, the elongated elastically stretchable members are fixed to the inner non-woven fabric layer 61 and the outer non-woven fabric layer 62, and the inner non-woven fabric layer 61 is fixed to the outer non-woven fabric layer 62, with only a hot-melt adhesive applied to the circumferential surfaces of the elastically stretchable gather members 63.

In the front-back unerected regions on the two edges of the leg-surrounding gathers 60 in the front-back direction, the inner non-woven fabric layer 61 and the outer non-woven fabric layer 62 can be bonded together, the leg-surrounding gathers 60 can be fixed to the front outer member 12F and the back outer member 12B, as illustrated in FIGS. 1 to 6, the proximal portions and the distal portions can be fixed in the leg-surrounding gathers 60, as illustrated in FIGS. 7 and 8, and the proximal portions and the distal portions can be fixed to the inner member 200, with at least one of the hot-melt adhesive through various application processes and a fixing means 67, such as heat sealing or ultrasonic sealing, through welding of the material. In the illustrated embodiments, the hot-melt adhesive and the fixing means 67 by welding of the materials are combined. Alternatively, only one of these means may be used for the fixing.

The dimensions of the leg-surrounding gathers 60 can be appropriately selected. For disposable baby diapers, the vertical length of each leg-surrounding gather 60 (the distance between the distal edge and the proximal edge in the width direction in a spread state) is in the range of 15 to 60 mm, preferably 20 to 40 mm.

In the embodiments described above, it is preferred that the inner non-woven fabric layer 61 and the outer non-woven fabric layer 62 be composed of soft, uniform non-woven fabric having satisfactory sealing properties, such as spunbond non-woven fabrics (SS, SSS), SMS non-woven fabrics (SMS, SSMMS), and meltblown non-woven fabrics, provided with a water repellent finish of silicone, for example, as required. The fiber basis weight is preferably within the range of approximately 10 to 30 g/m². With reference to FIGS. 3 and 4, it is apparent from the top sheet 30 constituting the inner non-woven fabric layer 61 closer to the proximal edges than the fabric-free sections 65 that the inner non-woven fabric layer 61 and the outer non-woven fabric layer 62 may each be partially composed of different materials. Alternatively, the inner non-woven fabric layer 61 and the outer non-woven fabric layer 62 may be composed of different materials.

In the embodiments described above, the elastically stretchable gather members 63 may be elongated elastically stretchable members, such as rubber threads or strips. The fineness of the rubber threads is preferably within the range of 470 to 1240 dtex, more preferably, 620 to 940 dtex. The elongation rate in a fixed state is preferably within the range of 150% to 350%, more preferably, 200% to 300%.

In the embodiments described above, one leg-surrounding gather 60 is disposed in each of the right and left regions. Alternatively, multiple leg-surrounding gathers 60 may be disposed.

Evaluation Test

Samples were prepared according to examples 1 and 2 described below, and 30 participants determined the samples having a softer texture in a natural length state.

Example 1

Two spunbond non-woven fabrics composed of polypropylene fiber (fineness 2.2 dtex, basis weight 15 g/m²) having a MD length of 100 mm and a CD length of 100 mm were prepared. A hot-melt adhesive of 10 g/m² in volume was applied on the two MD edges of a first sheet layer; rubber threads stretched at a stretch rate of 270% and having a fineness of 470 dtex were disposed in parallel with each other on the first sheet layer at 5-mm intervals 19d in the CD; a second sheet layer was disposed over the rubber threads with the MD and the CD aligned with those of the first sheet layer; an ultrasonic seal was then applied in a pattern substantially continuous in the MD (the pattern illustrated in FIG. 12) in the areas between adjacent elastically stretchable members; and the two sheet layers were bonded, to prepare a stretchable sheet sample in which the MD is the stretchable direction and the CD is the direction orthogonal to the stretchable direction. The dimensions and intervals of the sheet bonding sections were as follows:

Maximum length 20x of the sheet bonding sections in the stretchable direction: 1.57 mm
Maximum length 20y of the sheet bonding sections in the orthogonal direction: 0.70 mm
Interval 20t of the sheet bonding sections in the stretchable direction: 1.23 mm (0.78 times the maximum length 20x of the sheet bonding sections in the stretchable direction)
Interval 20d of the sheet bonding sections in the orthogonal direction: 0.70 mm (1.0 time the maximum length 20y of the sheet bonding sections in the orthogonal direction)
Overlapping width 20w of the sheet bonding sections in the stretchable direction: 0.17 mm (0.24 times the orthogonal direction interval 20d of the sheet bonding sections)
Length 20z of an area of the inter-free region including the sheet bonding sections in the orthogonal direction: 1.25 mm
Interval 20s of the sheet bonding sections in an adjacent inter-free region in the orthogonal direction: 6.75 mm Example 2

Another sample was prepared in the same manner as in Example 1 except that an ultrasonic seal was formed in a pattern illustrated in FIG. 17 where the dimensions and intervals of the sheet bonding sections 20 were as follows:
Dimensions of each sheet bonding section (length 20x in the stretchable direction×length 20y in the orthogonal direction): 0.8 mm×5.0 mm
Intervals 20r of the sheet bonding sections in the stretchable direction: 8.0 mm
Intervals 20v of the sheet bonding sections in the orthogonal direction: 3.0 mm
(Results of Evaluation)

All the 30 participants perceived the example to be softer than the comparative example.

Others (a) The material for the two sheet layers 12S and 12H can be appropriately selected. It is preferred that the material have a bending resistance in the stretchable direction higher than that in the direction orthogonal to the stretchable direction because the tops of the corrugations 80 can readily and gradually bend.

(b) It is preferred that the sheet bonding sections 20 be disposed in every area between the elastically stretchable members 19 adjacent to each other in the front-back direction, as in the illustrated embodiments. Alternatively, the sheet bonding sections 20 may be disposed in the areas between every several elastically stretchable members adjacent to each other. In specific, it is preferred that one elastically stretchable member 19 be disposed between every sheet bonding sections 20 adjacent to each other in the front-back direction. Alternatively, several elastically stretchable members 19 may be disposed.

(c) A single sheet bonding section 20 is disposed between two adjacent elastically stretchable members 19 in the front-back direction (the section substantially continuous is defined as one sheet bonding section 20) as in the illustrated embodiments. Alternatively, multiple sheet bonding sections 20 may be disposed, as illustrated in FIG. 14.

(d) In the illustrated embodiments, the present invention is applied to the entire stretchable structure in the width direction of the outer members 12F and 12B. Alternatively, the present invention may be applied to a portion of the stretchable structure, and the remaining portion (only the waist region, for example) may have a known stretchable structure in which a hot-melt adhesive is applied to only the circumferential surface of the entire elastically stretchable members 19 along the width direction and the elastically stretchable members 19 are fixed between the two sheet layers 12S and 12H. Alternatively, the present invention may be applied to only one of the front outer member 12F and the back outer member 12B.

Descriptions of Terms Used in Specification

The following terms used in the specification should be understood to have the meanings defined below unless otherwise defined in this specification.

"Front-back (longitudinal) direction" refers to the direction connecting the ventral (front) side and the dorsal (back) side, and "width direction" refers to the direction orthogonal to the front-back direction (right-left direction).

"Spread state" refers to a flat spread state without contraction or looseness.

"Stretch rate" refers to a value with respect to 100% representing a natural length state.

"Basis weight" is measured as follows. After preliminary drying of a sample or test piece, the sample or test piece is left in a test room or a test device under normal conditions (an ambient temperature of 20±5° C. and a relative humidity of 65% or less at the testing site) until the weight of the sample or test piece reaches constant mass. Preliminary drying is to achieve the constant mass of the sample or test piece under an environment having a relative humidity within the range of 10% to 25% and a temperature not exceeding 50° C. For fibers having a standard moisture regain of 0.0%, preliminary drying may be omitted. The test piece having constant mass is cut with a cutting template (200×250 mm, ±2 mm) into samples of 200×250 mm (±2 mm). The weight of the sample is measured. The measured weight is multiplied by 20 to determine the weight per square meter, which is defined as the basis weight.

"Thickness" is automatically measured with an automatic thickness gauge (KES-G5 handy compression tester) under a load of 10 gf/cm$^2$ in a pressurized area of 2 cm$^2$.

"Water absorption capacity" is measured in accordance with JIS K7223-1996 standard "Testing Method for Water Absorption Capacity of Superabsorbent Polymers."

"Water absorption rate" is defined as "time that elapses before the end point" measured with superabsorbent polymers (2 g) and a normal saline solution (50 g) in accordance with JIS K7224-1996 "Testing Method for Water Absorption Rate of Super Absorbent Polymers."

"Bending resistance" refers to "8.21.1 Method A (45° Cantilever Method)" of JIS L 1096:2010 "Testing Methods for Woven and Knitted Fabrics."

The tests and measurements are carried out in a laboratory or an apparatus under normal conditions (a temperature of 20±5° C. and a relative humidity of 65% or less at the testing site), unless the environmental condition for the tests and measurements are otherwise specified.

The dimensions of the components are measured in a spread state, not a natural length state, unless otherwise specified.

INDUSTRIAL APPLICABILITY

The present invention is suitable for underpants-type disposable diapers.

REFERENCE SIGNS LIST 11 liquid impervious sheet, 12A side seal portion, 12B back outer member, 12F, 12B outer member, 12F front outer member, 12H inner sheet layer, 12S, 12H two sheet layers, 12S outer sheet layer, 15, 18 under-waist elastically stretchable members, 16 cover elastically stretchable member, 17 waist elastically stretchable member, 19 elastically stretchable member, 19f fixed end, 19m free section, 20 sheet bonding section, 21 unbonded region, 30 top sheet, 40 intermediate sheet, 50 absorbent element, 56 absorber, 58 wrapping sheet, 60 leg-surrounding gather, 61 inner non-woven fabric layer, 62 outer non-woven fabric layer, 63 elastically stretchable gather member, 64 liquid impervious sheet, 65 fabric-free section, 66 gather sheet, 66r folded portion, 70 residual elastically stretchable member, 80 corrugation, 200 inner member, 201 inner-outer fixing portion, A1 non-stretchable region, A2 intermittent stretchable region, A3 continuous stretchable region, FA inter-free region.

The invention claimed is:
1. An underpants-type disposable diaper comprising:
an outer member disposed in a front body and a back body, the outer member comprising a single segment or two discrete segments, said outer member having a width, a front-back length, a thickness and two side edges; and an inner member disposed from the inner face of the outer member in the front body to an inner face of the outer member in the back body in an intermediate region in a width direction and including an absorber, wherein the two side edges of the outer member in the front body and the two side edges of the outer member in the back body are bonded together into side seal portions defining a waist opening and left and right leg openings, the outer member comprises a stretchable region adjacent to an inner edge of at least one of the side seal portions in the width direction, the stretchable region comprises two substantially coextensive stacked sheet layers extending in the width direction and a front-back longitudinal direction and a plurality of elongated elastically stretchable members extending in the width direction at predetermined intervals in the front-back longitudinal direction between the sheet layers, the elastically stretchable members each has two fixed ends fixed to the two sheet layers in a stretchable direction, and a free section between the fixed ends, the free section being unfixed to the two sheet layers, wherein the stretchable direction of the stretchable region is the width direction, the two sheet layers are welded to each other in a thickness direction to form at least one sheet bonding section in an inter-free region defined between two adjacent free sections in the front-back longitudinal direction, in the stretchable region, no sheet bonding section protrudes into the side seal portion, and wherein the sheet bonding section is substantially continuous in the width direction of the inter-free region in the stretchable region.

2. The underpants-type disposable diaper according to claim 1, wherein the sheet bonding section is substantially continuous to an across-the-width position of an intermediate position of the fixed end adjacent to the side seal portion in the width direction, and an end of said one or more sheet bonding section adjacent to the side seal portion is separated from the side seal portion.

3. The underpants-type disposable diaper according to claim 1, wherein at least the fixed end adjacent to the side seal portion is formed by bonding the two sheet layers together and by fixing the elastically stretchable members to the two sheet layers with a hot-melt adhesive continuing across the entire front-back length of the side seal portion.

4. The underpants-type disposable diaper according to claim 1, wherein at least the fixed end adjacent to the side seal portion is formed by bonding the two sheet layers together and by fixing the elastically stretchable members to the two sheet layers with a hot-melt adhesive continuing across the entire front-back length of the side seal portion.

5. The underpants-type disposable diaper according to claim 2, wherein at least the fixed end adjacent to the side seal portion is formed by bonding the two sheet layers together and by fixing the elastically stretchable members to the two sheet layers with a hot-melt adhesive continuing across the entire front-back length of the side seal portion.

* * * * *